(12) United States Patent
Haque

(10) Patent No.: US 6,667,315 B2
(45) Date of Patent: Dec. 23, 2003

(54) CARDIOPROTECTIVE PHOSPHONATES AND MALONATES

(75) Inventor: Wasimul Haque, Edmonton (CA)

(73) Assignee: Medicure International Inc., St. James (BA)

( * ) Notice: Subject to any disclaimer, the term of this patent is extended or adjusted under 35 U.S.C. 154(b) by 0 days.

(21) Appl. No.: 10/282,326

(22) Filed: Oct. 28, 2002

(65) Prior Publication Data

US 2003/0114678 A1 Jun. 19, 2003

Related U.S. Application Data

(62) Division of application No. 09/795,689, filed on Feb. 28, 2001.
(60) Provisional application No. 60/185,899, filed on Feb. 29, 2000.

(51) Int. Cl.$^7$ .................. A61K 31/4415; C07F 9/58; C07F 9/576
(52) U.S. Cl. .............................. 514/306; 546/22; 546/24
(58) Field of Search ....................... 546/22, 24; 514/306

(56) References Cited

U.S. PATENT DOCUMENTS

| | | | |
|---|---|---|---|
| 3,206,463 A | 9/1965 | Baetz .......................... 546/301 |
| 3,910,921 A | 10/1975 | Esanu .......................... 546/23 |
| 3,987,177 A | 10/1976 | Giudicelli et al. .......... 514/283 |
| 4,032,534 A | 6/1977 | Chodkiewicz .............. 548/201 |
| 4,036,844 A | 7/1977 | Thorne et al. .............. 546/290 |
| 4,053,607 A | 10/1977 | Thorne et al. .............. 514/345 |
| 4,137,316 A | 1/1979 | Esanu ........................... 514/76 |
| 4,167,562 A | 9/1979 | Evers .......................... 424/678 |
| 4,361,570 A | 11/1982 | Fici ............................ 514/358 |
| 4,369,172 A | 1/1983 | Schor et al. ................. 424/468 |
| 4,374,841 A | 2/1983 | Descamps et al. .......... 514/351 |
| 4,515,771 A | 5/1985 | Fine ............................ 424/52 |
| 4,567,179 A | 1/1986 | Lombardino ............. 514/226.5 |
| 4,569,938 A | 2/1986 | Esanu ........................... 514/302 |
| 4,569,939 A | 2/1986 | Esanu ........................... 514/302 |
| 4,581,363 A | 4/1986 | Esanu ........................... 546/202 |
| 4,605,741 A | 8/1986 | Zagnoli et al. ................ 546/24 |
| 4,696,920 A | 9/1987 | Bentzen et al. ............. 514/89 |
| 4,730,042 A | 3/1988 | Hege et al. ................. 514/124 |
| 4,735,950 A | 4/1988 | Esanu ......................... 514/345 |
| 4,735,956 A | 4/1988 | Baldwin et al. ............ 514/338 |
| 4,837,239 A | 6/1989 | Benjamin et al. .......... 514/267 |
| 4,843,071 A | 6/1989 | Hohenwarter .............. 514/217 |
| 4,962,121 A | 10/1990 | Hamberger et al. ........ 514/419 |
| 5,001,115 A | 3/1991 | Sloan ............................ 514/34 |
| 5,053,396 A | 10/1991 | Blass ........................... 514/45 |
| 5,118,505 A | 6/1992 | Költringer ................... 424/752 |
| 5,130,324 A | 7/1992 | Ulrich et al. ............... 514/357 |
| 5,132,115 A | 7/1992 | Wolter et al. ............... 424/448 |
| 5,210,083 A | 5/1993 | Pfirrmann ................... 514/222.5 |
| 5,213,813 A | 5/1993 | Kornecki et al. ........... 424/532 |
| 5,254,557 A | 10/1993 | Buckle et al. ............... 514/269 |
| 5,254,572 A | 10/1993 | Serfontein .................. 514/345 |
| 5,272,165 A | 12/1993 | Ulrich et al. ............... 514/357 |
| 5,278,154 A | 1/1994 | Lacoste et al. .............. 514/114 |
| 5,288,716 A | 2/1994 | Speck ........................... 514/89 |
| 5,326,757 A | 7/1994 | Demopoulos ............... 514/167 |
| 5,328,453 A | 7/1994 | Sibalis .......................... 604/20 |
| 5,372,999 A | 12/1994 | Schneider et al. ........... 514/81 |
| 5,385,937 A | 1/1995 | Stamler et al. .............. 514/557 |
| 5,420,112 A | 5/1995 | Lewis et al. ................. 514/12 |
| 5,441,972 A | 8/1995 | Ogata et al. ................. 514/342 |
| 5,504,090 A | 4/1996 | Neely ..................... 514/263.34 |
| 5,563,126 A | 10/1996 | Allen et al. ................... 514/52 |
| 5,569,459 A | 10/1996 | Shlyankevich .............. 424/728 |
| 5,569,648 A | 10/1996 | Lewis et al. ................. 514/12 |
| 5,631,271 A | 5/1997 | Serfontein ................... 514/345 |
| 5,633,228 A | 5/1997 | Lewis et al. ................. 514/12 |
| 5,648,335 A | 7/1997 | Lewis et al. ................. 514/12 |
| 5,728,684 A | 3/1998 | Cheng et al. ................ 514/50 |
| 5,733,884 A | 3/1998 | Barbul et al. ................ 512/21 |
| 5,733,916 A | 3/1998 | Neely ...................... 514/263.3 |
| 5,770,215 A | 6/1998 | Moshyedi ................... 424/440 |
| 5,795,873 A | 8/1998 | Allen ........................... 514/52 |
| 5,804,163 A | 9/1998 | Gibby et al. ............. 424/9.361 |
| 5,804,594 A | 9/1998 | Murad ......................... 514/474 |
| 5,833,998 A | 11/1998 | Biedermann et al. ....... 424/401 |
| 5,834,446 A | 11/1998 | Dow et al. .................. 514/58 |
| 5,840,685 A | 11/1998 | Fujii et al. .................... 514/12 |
| 5,847,008 A | 12/1998 | Doebber et al. ............ 514/708 |
| 5,858,017 A | 1/1999 | Demopoulos et al. ..... 604/890.1 |
| 5,859,051 A | 1/1999 | Adams et al. ............... 514/469 |
| 5,874,420 A | 2/1999 | Pelleg ........................... 514/81 |
| 5,874,443 A | 2/1999 | Kiely et al. ................. 514/309 |
| 5,888,514 A | 3/1999 | Weisman ................... 424/94.1 |
| 5,944,020 A | 8/1999 | Markov et al. ............. 128/898 |
| 6,043,259 A | 3/2000 | Dhalla et al. ............... 514/345 |

FOREIGN PATENT DOCUMENTS

| | | |
|---|---|---|
| BE | 831350 | 1/1976 |
| BE | 863754 | 5/1978 |

(List continued on next page.)

OTHER PUBLICATIONS

Arbuzov, S., "Synthesis and Pharmacological Investigation of Some New Compounds Related Structurally to Some Natural Metabolites", *Conf. Hug. Ther. Invest. Pharmacol., Soc. Pharmacol. Hung.*, pp. 489–502 (1966) (Abstract only).

Arbuzov, S., "Pharmacological Properties of the Products of the Condensation of Phenamine with Some Metabolites", *Farmakol. Toksikol.*, vol. 31, No. 3, pp. 373–376 (1968) (Abstract only).

(List continued on next page.)

*Primary Examiner*—Rita Desai
(74) *Attorney, Agent, or Firm*—Merchant & Gould P.C.

(57) ABSTRACT

The present invention provides for pyridoxine phosphonate analogues such as, for example, ((2-methyl-3-hydroxy-4-hydroxymethyl-5-pyridyl)alkylphosphonates, and (2-methyl-3-hydroxy-4-hydroxymethyl-5-pyridyl) azaalkylphosphonates) and to pyridoxine malonate analogues, such as, for example, ((2-methyl-3-hydroxy-4-hydroxymethyl-5-pyridylmethyl)malonates), pharmaceutical compositions, and methods for treatment of cardiovascular and related diseases, and diabetes mellitus and related diseases.

9 Claims, No Drawings

FOREIGN PATENT DOCUMENTS

| | | |
|---|---|---|
| CH | 561 183 | 4/1975 |
| DE | 1 958 226 | 5/1970 |
| DE | 24 61 742 A | 7/1976 |
| DE | 37 05 549 A1 | 9/1988 |
| DE | 43 44 751 A1 | 6/1995 |
| EP | 0 121 036 A1 | 10/1984 |
| EP | 0 144 051 A2 | 6/1985 |
| EP | 0 270 026 A2 | 6/1988 |
| EP | 0 416 248 A2 | 3/1991 |
| EP | 0 891 719 A1 | 1/1999 |
| FR | 846376 | 3/1941 |
| FR | 1323941 | 12/1963 |
| FR | 5552 M | 12/1967 |
| FR | 5801 M | 3/1968 |
| FR | 6453 M | 12/1968 |
| FR | 1579544 | 8/1969 |
| FR | 2 034 539 | 12/1970 |
| FR | 2101010 | 3/1972 |
| FR | 2255883 | 7/1975 |
| FR | 2428640 | 1/1980 |
| GB | 1 013 939 | 12/1965 |
| GB | 1172800 | 12/1969 |
| GB | 1 201 014 | 8/1970 |
| GB | 1 297 080 | 11/1972 |
| GB | 1 360 536 | 7/1974 |
| GB | 1 493 993 | 12/1977 |
| GB | 2 254 556 A | 10/1992 |
| JP | 48-21959 | 7/1973 |
| JP | 54-17130 | 2/1979 |
| JP | 10-158244 | 6/1998 |
| JP | 2000-26295 | 1/2000 |
| WO | WO 83/00085 | 1/1983 |
| WO | WO 91/19500 | 12/1991 |
| WO | WO 94/18965 | 9/1994 |
| WO | WO 98/28310 | 7/1998 |
| WO | WO 99/03365 | 1/1999 |
| WO | WO 99/53928 | 10/1999 |

OTHER PUBLICATIONS

Aybak, M. et al., "Effect of Oral Pyridoxine Hydrochloride Supplementation on Arterial Blood Pressure in Patients with Essential Hypertension", Drug Res., vol. 45, No. 12, pp. 1271–1273 (1995).

"B Vitamins May Cut Heart Disease Risk", Harvard Health Letter, 1 page (1998).

Baliga, B. et al., "Hyperhomocysteinemia in Type 2 Diabetes Mellitus: Cardiovascular Risk Factors and Effect of Treatment with Folic Acid and Pyridoxine", Endocrine Practice, vol. 6, No. 6, pp. 435–441 (Nov./Dec. 2000).

Barrett, S., "Homocysteine: A Cardiovascular Risk Factor Worth Considering", http://www.quackwatch.com/03HealthPromotion/homocysteine.html, 2 pages (©1997).

Bennett et al., "Vitamin $B_6$—Phosphonic Acids", J. of Med. and Pharm. Chem., vol. 1, No. 3, pp. 213–221 (1959).

Berger, A.R. et al., "Dose response, coasting, and differential fiber vulnerability in human toxic neuropathy: A prospective study of pyridoxine neurotoxicity", Neurology, vol. 42, No. 7, pp. 1367–1370 (Jul. 1992).

Bernstein, A., "Vitamin $B_6$ in Clinical Neurology", Annals of New York Academy of Sciences, vol. 585, pp. 250–260 (1990).

Bhagavan, H. et al., "Effect of Postweanling Pyridoxine Deficiency on Growth and Concentration of the Coenzyme Pyridoxal–5'–phosphate in Heart, Kidneys, Lungs, and Adrenals in Rats", Pediat. Res., vol. 10, pp. 730–732 (1976).

Bode, W. et al, "Pyridoxal–5'–Phosphate and Pyridoxal Biokinetics in Male Wistar Rats Fed Graded Levels of Vitamin B–6", J. Nutr., vol. 121, No. 11, pp. 1738–1745 (Nov. 1991).

Chasan–Taber, L. et al., "A Prospective Study of Folate and Vitamin $B_6$ and Risk of Myocardial Infarction in US Physicians", Journal of the American College of Nutrition, vol. 15, No. 2, pp. 136–143 (Apr. 1996).

Cho, Y. et al., "In Vivo Evidence for a Vitamin B–6 Requirement in Carnitine Synthesis", J. Nutr., vol. 120, pp. 258–265 (1990).

"Computer Generated Search Reports", 70 pages (May 1999).

Ebadi, M. et al., "Convulsant Activity of Pyridoxal Sulphate and Phosphonoethyl Pyridoxal: Antagonism by GABA and its Synthetic Analogues", Neuropharmacology, vol. 22, No. 7, pp. 865–873 (1983).

Ellis, J. et al., "Prevention of Myocardial Infarction of Vitamin $B_6$", Res. Commun. Molec. Pathol. Pharmacol., vol. 89, No. 2, pp. 208–220 (Aug. 1995).

Folsom, A. et al., "Clinical Investigation and Reports: Prospective Study of Coronary Heart Disease Incidence in Relation to Fasting Total Homocysteine, Related Genetic Polymorphisms, and B Vitamins: The Atherosclerosis Risk in Communities (ARIC) Study", Circulation, vol. 98, pp. 204–210 (Jul. 21, 1998).

Fonda, M., "Interaction of Pyridoxal Analogues with Glutamate Apodecarboxylase and Aspartate Apoaminotransferase", The Journal of Biological Chemistry, vol. 246, No. 7, pp. 2230–2240 (Apr. 10, 1971).

Harada, K. et al., "Studies on Vitamin $B_6$. (IV) Behavior of Pyridoxal Acylates in the Body After Parenteral Administration", Vitamins Journal of the Vitamin Society of Japan, vol. 45, No. 2, pp. 69–75 (Feb. 1972).

Hathcock, J., "Vitamins and minerals: efficacy and safety", Am J Clin Nutr, vol. 66, pp. 427–437 (1997).

Hoover, D.M. et al., "Ultrastructural Lesions of Pyridoxine Toxicity in Beagle Dogs", Vet. Pathol., vol. 18, pp. 769–777 (1981).

Kim, Y. et al., "Synthesis and Structure–Activity Relationships of Pyridoxal–6–arylazo–5'–phosphate and Phosphonate Derivatives as P2 Receptor Antagonists", Drug Development Research, vol. 45, pp. 52–66 (1998).

Kok, F. et al., "Low Vitamin $B_6$ Status in Patients with Acute Myocardial Infarction", Am. J. Cardiol., vol., 63, pp. 513–516 (Mar. 1, 1989).

Korytnyk et al., "Schiff Bases of Pyriodoxal: Their Structure and the Stabilization of their Ring–Chain Tautomeric Forms by Acylation, Tetrahedron", 26 (23), 5415–25.

Korytnyk, W., "Pyridoxine Chemistry. VI. Homologs of Pyridoxol and of 5–Pyridoxic Acid", Dept. of Exp. Therapeutics, Roswell Park Memorial Institute, Buffalo, New York, vol. 8, pp. 112–115 (1965).

Korytnyk. W., et al "Synthesis and Antagonist Properties of Pyridoxol Analogs Modified in the 5 Position", Pyridoxal Analogs, Dept. of Exp. Therapeutics, Roswell Park Memorial Institute, Buffalo, New York, vol. 10, pp. 345–350 (May 1967).

Krinke, G. et al., "Pyridoxine Megavitaminosis: An Analysis of the Early Changes Induced with Massive Doses of Vitamin $B_6$ in Rat Primary Sensory Neurons", *J. Neuropathol. Exp. Neurol.*, vol. 44, No. 7, pp. 117–129 (Mar. 1985).

Kubyshkin, V. et al., "Comparative characteristics of the arrhythmic syndrome and the possibility for its coenzyme correction in dilated and hypertrophic cardiomyopathy", *Abstract*, 1 pg. (1989).

Lal, K. et al., "Hypotensive action of 5–HT receptor agonists in the vitamin $B_6$–deficient hypertensive rat", *Eur. J. Pharmacol.*, vol. 234, Nos. 2/3, pp. 183–189 (Apr. 1993).

Lal, K. et al., "Calcium channels in vitamin $B_6$ deficiency–induced hypertension", *Journal of Hypertension*, vol. 11, No. 12, pp. 1357–1362 (Dec. 1993).

Lal, K. et al., "The effect of vitamin $B_6$ on the systolic blood pressure of rats in various animal models of hypertension", *Journal of Hypertension*, vol. 14, No. 3, pp. 355–363 (Mar. 1996).

Levy, H. et al., "Pyrodoxine Deficiency in Congestive Heart Failure", *P.S.E.B.M.*, vol. 101, pp. 617–621 (1959).

Manore, M. et al., "Changes In Plasma Pyridoxal Phosphate (PLP) In Diabetic (D), Hypertensive (HTN) and Hypertensive–diabetic (HTN–D) Men Fed A Constant Vitamin B–6 (B6) Diet", *Source Unknown*, pp. 1254 (Date Unknown).

Markov, A. et al, "Hemodynamic, electrocardiographic, and metabolic effects of fructose diphosphate on acute myocardial ischemia", *American Heart Journal*, vol. 100, No. 5, pp. 639–646 (Nov. 1980).

Mendelsohn, A. et al., "Hemodynamic and Clinical Effects of Oral Levodopa in Children With Congestive Heart Failure", *JACC*, vol. 30, No. 1, pp. 237–242 (Jul. 1997).

Merrill, Jr. et al. A. et al., "Diseases associated with defects in vitamin $B_6$ metabolism or utilization", *Ann. Rev. Nutr.*, vol. 7, pp. 137–156 (1987).

Miura, R. et al., "Reactions of Phosphonate Analogs of Pyridoxal Phosphate with Apo–aspartate Aminotransferase", *Archives of Biochemistry and Biophysics*, vol. 270, No. 2, pp. 526–540 (1989).

Mulvaney, D. et al., "Electrocardiographic changes in vitamin $B_6$ deficient rats", *Cardiovascular Research*, vol. 13, pp. 506–513 (1979).

Omenn, G. et al., "Preventing Coronary Heart Disease", *Circulation*, vol. 97, pp. 421–424 (1998).

Paulose, C. et al., "Sympathetic Stimulation and Hypertension in the Pyridoxine–Deficient Adult Rat", *Hypertension*, vol. 11, No. 4, pp. 387–391 (Apr. 1988).

Rao, R. et al., "Failure of Pyridoxine to Improve Glucose Tolerance in Diabetics", *Journal of Clinical Endocrinology & Metabolism*, vol. 50, No. 1, pp. 198–200 (Jan. 1980).

Rimm, E. et al., "Folate and Vitamin $B_6$ From Diet and Supplements in Relation to Risk of Coronary Heart Disease Among Women", *JAMA*, vol. 279, No. 5, pp. 359–364 (Feb. 4, 1998).

Sakuragi, T. et al., "The Synthesis of Long Chain Fatty Acid Derivatives of the Vitamin $B_6$ Group", *J. Am. Chem. Soc.*, vol. 78, pp. 839–842 (Feb. 20, 1956).

Sethi, R. et al., "Differential changes in left and right ventricular adenylyl cyclase activities in congestive heart failure", *The American Physiological Society*, vol. 272, No. 2, Part 2 of Two Parts, pp. H884–H893 (Feb. 1997).

Sethi, R. et al., "Inotropic Responses to Isoproterenol in Congestive Heart Failure Subsequent to Myocardial Infarction in Rats", *Journal of Cardiac Failure*, vol. 1, No. 5, pp. 391–399 (Dec. 1995).

Stirtan, W. et al., "Phosphonate and α–Fluorophosphonate Analogue Probes of the Ionization State of Pyridoxal 5'–Phosphate (PLP) in Glycogen Phosphorylase", *Biochemistry*, vol. 35, No. 47, pp. 15057–15064 (1996).

Takuma, Y. et al., "Combination Therapy of Infantile Spasms With High–Dose Pyridoxal Phosphate and Low–Dose Corticotropin", *Journal of Child Neurology*, vol. 11, No. 1, pp. 35–40 (Jan. 1996).

Tanaka, T. et al., "Pyridoxine Derivatives", *Chemical Abstracts*, vol. 62, No. 12, 1 page (Jun. 7, 1965).

Tomita, I. et al., "Synthesis of Vitamin $B_6$ Derivatives. II 3–Hydroxy–4–Hydroxymethyl–2–Methyl–5–Pyridine Acetic Acid and Related Substances", *Dept. of Biochem. and Biophys.*, Iowa Sate Univ., vol. 3, pp. 178–183 (Mar. 19, 1966).

Trezise, D. et al., "$P_2$ purinoceptor antagonist properties of pyridoxal–5–phosphate", *Eur. J. Pharmacol.*, vol. 259, No. 3, pp. 295–300 (Jul. 11, 1994).

Vanderjagt, D. et al., "Vitamin $B_6$ Status in a Healthy Elderly Population", *Annals New York Academy of Sciences*, pp. 562–564 (date unknown).

Verhoef, P. et al., "A Common Mutation in the Methylenetetrahydrofolate Reductase Gene and Risk of Coronary Heart Disease: Results Among U.S. Men", *JACC*, Vo. 32, No. 2, pp. 353–359 (Aug. 1998).

Verhoef, P. et al., "Homocysteine Metabolism and Risk of Myocardial Infarction: Relation with Vitamins $B_6$, $B_{12}$, and Folate", *Am. J. Epidemiol.*, vol. 143, No. 9, pp. 845–859 (May 1, 1996).

Vermaak, W.J.H. et al., "Vitamin $B_6$ and coronary artery disease. Epidemiological observations and case studies", *Atherosclerosis*, vol. 63, pp. 235–238 (Feb. 1987).

Vidrio, H., "Interaction with Pyridoxal as a Possible Mechanism of Hydralazine Hypotension", *Journal of Cardiovascular Pharmacology*, vol. 15, pp. 150–156 (1990).

Viscontini, V. et al., "Über einige Derivate des Pyridoxals", *Helvetica Chimica Acta*, vol. 34, No. 296, pp. 2438–2439 (1951).

Windebank, A., "Neurotoxicity of Pyridoxine Analogs Is Related to Coenzyme Structure", *Neurochemical Pathology*, vol. 3, pp. 159–167 (1985).

Yan, S. et al., "A Role for Pyridoxal Phosphate in the Control of Dephosphorylation of Phosphorylase α", *J. of Biological Chem.*, vol. 254, No. 17, pp. 8263–8269 (Sep. 10, 1979).

Yarat, A. et al., "Effect of vitamin B6 on lenses of diabetic rats", *Indian Journal of Experimental Biology*, vol. 36, pp. 1269–1272 (Dec. 1998).

Zempleni, J. et al., "The utiliation of intravenously infused pyridoxine in humans", *Clinica Chimica Acta*, vol. 229, Nos. 1, 2, pp. 27–36 (Sep. 1994).

CARDIOPROTECTIVE PHOSPHONATES AND MALONATES

PRIORITY OF INVENTION

This application is a divisional of application Ser. No. 09/795,689, filed Feb. 28, 2001, which claims priority of invention under 35 U.S.C. §119(e) from U.S. provisional application No. 60/185,899, Feb. 29, 2000.

FIELD OF THE INVENTION

This invention relates to pyridoxine phosphonate analogues, to pyridoxine malonate analogues, to their preparation, to pharmaceutical compositions thereof, and to treatments for cardiovascular and related diseases, for example, hypertrophy, hypertension, congestive heart failure, myocardial ischemia, arrhythmia, heart failure subsequent to myocardial infarction, myocardial infarction, ischemia reperfusion injury, and diseases that arise from thrombotic and prothrombotic states in which the coagulation cascade is activated; and treatments for diabetes mellitus and related diseases, for example, hyperinsulinemia, diabetes-induced hypertension, obesity, insulin resistance, and damage to blood vessels, eyes, kidneys, nerves, autonomic nervous system, skin connective tissue, or immune system.

BACKGROUND

Pyridoxal-5'-phosphate (PLP), an end product of vitamin $B_6$ metabolism, plays a vital role in mammalian health. In previous patents (U.S. Pat. Nos. 6,051,587 and 6,043,259, herein incorporated by reference) the role of pyridoxal-5'-phosphate, and its precursors pyridoxal and pyridoxine (vitamin $B_6$), in mediating cardiovascular health and in treating cardiovascular related diseases is disclosed.

The major degradation pathway for pyridoxal-5'-phosphate in vivo is the conversion to pyridoxal, catalysed by alkaline phosphatase. Thus, there is a need to identify and administer drugs that are functionally similar to pyridoxal-5'-phosphate such as pyridoxine phosphonate analogues or pyridoxine malonate analogues, that elicit similar or enhanced cardiovascular benefits, and that beneficially affect PLP-related conditions, but are stable to degradation by phosphatase.

SUMMARY OF THE INVENTION

The present invention provides for pyridoxine phosphonate analogues and to pyridoxine malonates. In one aspect, the present invention includes a compound of formula I:

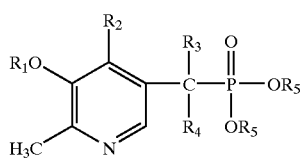

I in which $R_1$ is hydrogen or alkyl;

$R_2$ is —CHO, —$CH_2OH$, —$CH_3$, —$CO_2R_6$ in which $R_6$ is hydrogen, alkyl, or aryl; or $R_2$ is —$CH_2$-O-alkyl- in which alkyl is covalently bonded to the oxygen at the 3-position instead of $R_1$;

$R_3$ is hydrogen and $R_4$ is hydroxy, halo, alkoxy, alkylcarbonyloxy, alkylamino or arylamino; or $R_3$ and $R_4$ are halo; and $R_5$ is hydrogen, alkyl, aryl, aralkyl, or —$CO_2R_7$ in which $R_7$ is hydrogen, alkyl, aryl, or aralkyl;

or a pharmaceutically acceptable acid addition salt thereof.

In another aspect, the present invention includes a compound of formula II:

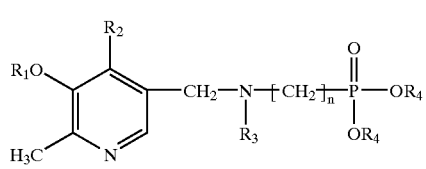

II in which $R_1$ is hydrogen or alkyl;

$R_2$ is —CHO, —$CH_2OH$, —$CH_3$ or —$CO_2R_5$ in which $R_5$ is hydrogen, alkyl, or aryl; or $R_2$ is —$CH_2$-O-alkyl- in which alkyl is covalently bonded to the oxygen at the 3-position instead of $R_1$;

$R_3$ is hydrogen, alkyl, aryl, or aralkyl;

$R_4$ is hydrogen, alkyl, aryl, aralkyl, or —$CO_2R_6$ in which $R_6$ is hydrogen, alkyl, aryl, or aralkyl; and n is 1 to 6;

or a pharmaceutically acceptable acid addition salt thereof.

In another aspect, the present invention includes a compound of formula III:

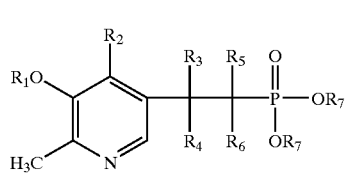

III in which $R_1$ is hydrogen or alkyl;

$R_2$ is —CHO, —$CH_2OH$, —$CH_3$ or —$CO_2R_8$ in which $R_8$ is hydrogen, alkyl, or aryl; or $R_2$ is —$CH_2$-O-alkyl- in which alkyl is covalently bonded to the oxygen at the 3-position instead of $R_1$;

$R_3$ is hydrogen and $R_4$ is hydroxy, halo, alkoxy or alkylcarbonyloxy; or $R_3$ and $R_4$ can be taken together to form =O;

$R_5$ and $R_6$ are hydrogen; or $R_5$ and $R_6$ are halo; and $R_7$ is hydrogen, alkyl, aryl, aralkyl, or —$CO_2R_8$ in which $R_8$ is hydrogen, alkyl, aryl, or aralkyl;

or a pharmaceutically acceptable acid addition salt thereof.

In another aspect, the present invention includes a compound of formula IV:

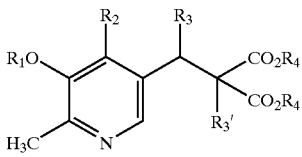

IV in which
R₁ is hydrogen or alkyl;
R₂ is —CHO, —CH₂OH, —CH₃ or CO₂R₅ in which R₅ is hydrogen, alkyl, or aryl; or
R₂ is —CH₂-O-alkyl- in which alkyl is covalently bonded to the oxygen at the 3-position instead of R₁;
R₃ and R₃' are independently hydrogen or halo; or
R₃ and R₃' taken together constitute a second covalent bond between the carbons to which they are substituent; and
R₄ is hydrogen or alkyl;
or a pharmaceutically acceptable acid addition salt thereof.

In another aspect, the invention is directed to pharmaceutical compositions that include a pharmaceutically acceptable carrier and a therapeutically effective amount of at least one compound of formula I, II, III or IV.

In another aspect, the invention is directed to a method of treating cardiovascular and related diseases, for example, hypertension, hypertrophy, arrhythmia, congestive heart failure, myocardial ischemia, heart failure subsequent to myocardial infarction, myocardial infarction, ischemia reperfusion injury, and diseases that arise from thrombotic and prothrombotic states in which the coagulation cascade is activated by administering a therapeutically effective amount of at least one compound of formula I, II, III or IV in a unit dosage form. For such a method, a compound of formula I, II, III or IV can be administered alone or concurrently with a known therapeutic cardiovascular agent, for example, angiotensin converting enzyme inhibitor, an angiotensin II receptor antagonist, a vasodilator, a diuretic, an α-adrenergic receptor antagonist, a β-adrenergic receptor antagonist, an antioxidant, or a mixture thereof.

In still another aspect, the invention is directed to a method of treating diabetes mellitus and related diseases, for example, hyperinsulinemia, insulin resistance, obesity, diabetes-induced hypertension, and damage to eyes, kidneys, blood vessels, nerves, autonomic nervous system, skin, connective tissue, or immune system, by administering a therapeutically effective amount of a compound of formula I, II, III or IV in a unit dosage form. For such a method, a compound of formula I, II, III or IV can be administered alone or concurrently with known medicaments suitable for treating diabetes mellitus and related diseases, for example, insulin, hypoglycemic drugs, or a mixture thereof.

DESCRIPTION OF THE INVENTION

The present invention provides for pyridoxine phosphonate analogues such as, for example, ((2-methyl-3-hydroxy-4-hydroxymethyl-5-pyridyl)alkylphosphonates, and (2-methyl-3-hydroxy-4-hydroxymethyl-5-pyridyl) azaalkylphosphonates) and to pyridoxine malonate analogues, such as, for example, ((2-methyl-3-hydroxy-4-hydroxymethyl-5-pyridylmethyl)malonates), pharmaceutical compositions, and methods for treatment of cardiovascular and related diseases, and diabetes mellitus and related diseases.

It is to be understood that the recitation of numerical ranges by endpoints includes all numbers and fractions subsumed within that range (e.g. 1 to 5 includes 1, 1.5, 2, 2.75, 3, 3.80, 4, and 5).

It is to be understood that all numbers and fractions thereof are presumed to be modified by the term "about."

It is to be understood that "a," "an," and "the" include plural referents unless the content clearly dictates otherwise. Thus, for example, reference to a composition containing "a compound" includes a mixture of two or more compounds.

It is to be understood that some of the compounds described herein contain one or more asymmetric centers and may thus give rise to enantiomers, diasteriomers, and other stereoisomeric forms which may be defined in terms of absolute stereochemistry as (R)— or (S)—. The present invention is meant to imclude all such possible diasteriomers and enantiomers as well as their racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and A geometric isomers. Likewise all tautomeric forms are intended to be included.

The general definitions used herein have the following meanings within the scope of the present invention.

As used herein the term "alkyl" includes a straight or branched saturated aliphatic hydrocarbon redicals, such as, for example, methyl, ethyl, propyl, isopropyl (1-methylethyl),

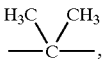

butyl, tert-butyl (1,1-dimethylethyl), and the like.

As used herein the term "alkoxy" refers to —O-alkyl with alkyl as defined above. Alkoxy groups include those with 1 to 4 carbon atoms in a straight or branched chain, such as, for example, methoxy, ethoxy, propoxy, isopropoxy (1-methylethoxy), butoxy, tert-butoxy (1,1-dimethylethoxy), and the like.

As used herein the term "aryl" refers to unsaturated aromatic carbocyclic radicals having a single ring, such as phenyl, or multiple condensed rings, such as naphthyl or anthryl. The term "aryl" also includes substituted aryl comprising aryl substituted on a ring by, for example, $C_{1-4}$ alkyl, $C_{1-4}$ alkoxy, amino, hydroxy, phenyl, nitro, halo, carboxyalkyl or alkanoyloxy. Aryl groups include, for example, phenyl, naphthyl, anthryl, biphenyl, methoxyphenyl, halophenyl, and the like.

As used herein the term "alkylamino" refers to —N-alkyl with alkyl as defined above. Alkylamino groups include those with 1–6 carbons in a straight or branched chain, such as, for example, methylamino, ethylamino, propylamino, and the like.

As used herein the term "arylamino" refers to —N-aryl with aryl as defined above. Arylamino includes —NH-phenyl, —NH-biphenyl, —NH-4-methoxyphenyl, and the like.

As used herein the term "aralkyl" refers to an aryl radical defined as above substituted with an alkyl radical as defined above (e.g. aryl-alkyl-). Aralkyl groups include, for example, phenethyl, benzyl, and naphthylmethyl.

As used herein the term "halo" includes bromo, chloro, and fluoro. Preferably halo is fluoro.

As used herein the term "alkylcarbonyloxy" includes alkyl as defined above bonded to carbonyl bonded to oxygen, such as, for example, acetate, propionate and t-butylcarbonyloxy.

Cardiovascular and related diseases include, for example, hypertension, hypertrophy, congestive heart failure, heart failure subsequent to myocardial infarction, arrhythmia, myocardial ischemia, myocardial infarction, ischemia reperfusion injury, and diseases that arise from thrombotic and prothrombotic states in which the coagulation cascade is activated.

Heart failure is a pathophysiological condition in which the heart is unable to pump blood at a rate commensurate with the requirement of the metabolizing tissues or can do so only from an elevated filling pressure (increased load). Thus, the heart has a diminished ability to keep up with its workload. Over time, this condition leads to excess fluid accumulation, such as peripheral edema, and is referred to as congestive heart failure.

When an excessive pressure or volume load is imposed on a ventricle, myocardial hypertrophy (i.e., enlargement of the heart muscle) develops as a compensatory mechanism. Hypertrophy permits the ventricle to sustain an increased load because the heart muscle can contract with greater force. However, a ventricle subjected to an abnormally elevated load for a prolonged period eventually fails to sustain an increased load despite the presence of ventricular hypertrophy, and pump failure can ultimately occur.

Heart failure can arise from any disease that affects the heart and interferes with circulation. For example, a disease that increases the heart muscle's workload, such as hypertension, will eventually weaken the force of the heart's contraction. Hypertension is a condition in which there is an increase in resistance to blood flow through the vascular system. This resistance leads to increases in systolic and/or diastolic blood pressures. Hypertension places increased tension on the left ventricular myocardium, causing it to stiffen and hypertrophy, and accelerates the development of atherosclerosis in the coronary arteries. The combination of increased demand and lessened supply increases the likelihood of myocardial ischemia leading to myocardial infarction, sudden death, arrhythmias, and congestive heart failure.

Ischemia is a condition in which an organ or a part of the body fails to receive a sufficient blood supply. When an organ is deprived of a blood supply, it is said to be hypoxic. An organ will become hypoxic even when the blood supply temporarily ceases, such as during a surgical procedure or during temporary artery blockage. Ischemia initially leads to a decrease in or loss of contractile activity. When the organ affected is the heart, this condition is known as myocardial ischemia, and myocardial ischemia initially leads to abnormal electrical activity. This can generate an arrhythmia. When myocardial ischemia is of sufficient severity and duration, cell injury can progress to cell death—i.e., myocardial infarction—and subsequently to heart failure, hypertrophy, or congestive heart failure.

When blood flow resumes to an organ after temporary cessation, this is known as ischemic reperfusion of the organ. For example, reperfusion of an ischemic myocardium can counter the effects of coronary occlusion, a condition that leads to myocardial ischemia. Ischemic reperfusion to the myocardium can lead to reperfusion arrhythmia or reperfusion injury. The severity of reperfusion injury is affected by numerous factors, such as, for example, duration of ischemia, severity of ischemia, and speed of reperfusion. Conditions observed with ischemia reperfusion injury include neutrophil infiltration, necrosis, and apoptosis.

Drug therapies, using known active ingredients such as vasodilators, angiotensin II receptor antagonists, angiotensin converting enzyme inhibitors, diuretics, antithrombolytic agents, α or β-adrenergic receptor antagonists, α-adrenergic receptor antagonists, calcium channel blockers, and the like, are available for treating cardiovascular and related diseases.

Diabetes mellitus and related diseases include hyperinsulinemia, insulin resistance, obesity, diabetes-induced hypertension, and damage to blood vessels, eyes, kidneys, nerves, autonomic nervous system, skin, connective tissue, and immune system. Diabetes mellitus is a condition in which blood glucose levels are abnormally high because the body is unable to produce enough insulin to maintain normal blood glucose levels or is unable to adequately respond to the insulin produced. Insulin-dependent diabetes mellitus (often referred to as type I diabetes) arises when the body produces little or no insulin. About 10% of all diabetics have type I diabetes. Noninsulin-dependent diabetes mellitus (often referred to as type II diabetes) arises when the body cannot adequately respond to the insulin that is produced in response to blood glucose levels.

Available treatments include weight control, exercise, diet, and drug therapy. Drug therapy for type I diabetes mellitus requires the administration of insulin; however, drug therapy for type II diabetes mellitus usually involves the administration of insulin and/or oral hypoglycemic drugs to lower blood glucose levels. If the oral hypoglycemic drugs fail to control blood sugar, then insulin, either alone or concurrently with the hypoglycemic drugs, will usually be administered.

The invention is generally directed to pyridoxine phosphonate analogues such as, for example, ((2-methyl-3-hydroxy-4-hydroxymethyl-5-pyridyl)alkylphosphonates, (2-methyl-3-hydroxy-4-hydroxymethyl-5-pyridyl) azaalkylphosphonates) and to pyridoxine malonate analogues such as, for example, ((2-methyl-3-hydroxy-4-hydroxymethyl-5-pyridylmethyl)malonates), compositions including these analogues, and methods of administering pharmaceutical compositions containing a therapeutically effective amount of at least one of these analogues to treat cardiovascular and related diseases or diabetes and related diseases.

To enhance absorption from the digestive tract and across biological membranes, polar groups on a drug molecule can be blocked with lipophilic functions that will be enzymatically cleaved off from the drug after absorption into the circulatory system. Lipophilic moieties can also improve site-specificity and bioavailability of the drug. The speed at which the blocking groups are removed can be used to control the rate at which the drug is released. The blocking of polar groups on the drug can also slow first-pass metabolism and excretion. An ester is a common blocking group that is readily hydrolyzed from the drug by endogenous esterases. Bundgaard, *Design and Application of Prodrugs* in *A Textbook of Drug Design and Development* (Krogsgaard-Larson & Bundgaard, eds., Hardwood Academic Publishers, Reading, United Kingdom 1991).

In one embodiment, the compounds of the present invention are analogues of pyridoxal phosphonate. The compounds of the invention include, for example, (2-methyl-3-hydroxy-4-hydroxymethyl-5-pyridyl)methylphosphonate analogues. Such compounds are represented by the formula I:

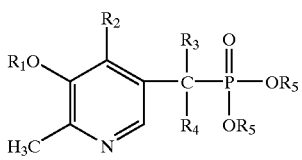

I in which
R$_1$ is hydrogen or alkyl;
R$_2$ is —CHO, —CH$_2$OH, —CH$_3$, —CO$_2$R$_6$ in which R$_6$ is hydrogen, alkyl, or aryl; or
R$_2$ is —CH$_2$-O-alkyl- in which alkyl is covalently bonded to the oxygen at the 3-position instead of R$_1$;
R$_3$ is hydrogen and R$_4$ is hydroxy, halo, alkoxy, alkylcarbonyloxy, alkylamino or arylamino; or
R$_3$ and R$_4$ are halo; and
R$_5$ is hydrogen, alkyl, aryl, aralkyl, or —CO$_2$R$_7$ in which R$_7$ is hydrogen, alkyl, aryl, or aralkyl;
or a pharmaceutically acceptable acid addition salt thereof.

Examples of compounds of formula I include those where R$_1$ is hydrogen, or those where R$_2$ is —CH$_2$OH, or —CH$_2$-O-alkyl- in which alkyl is covalently bonded to the oxygen at the 3-position instead of R$_1$, or those where R$_3$ is hydrogen and R$_4$ is F, MeO— or CH$_3$C(O)O—, or those where R$_5$ is alkyl or aralkyl. Additional examples of compounds of formula I include those where R$_3$ and R$_4$ are F, or those where R$_5$ is t-butyl or benzyl.

In another aspect, the compounds of the invention include (2-methyl-3-hydroxy-4-hydroxymethyl-5-pyridyl) azaalkylphosphonate analogues. Such compounds are represented by formula II:

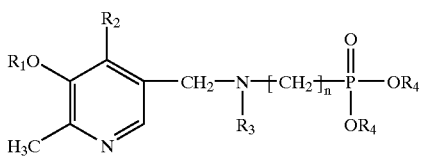

II in which
R$_1$ is hydrogen or alkyl;
R$_2$ is —CHO, —CH$_2$OH, —CH$_3$ or —CO$_2$R$_5$ in which R$_5$ is hydrogen, alkyl, or aryl; or
R$_2$ is —CH$_2$-O-alkyl- in which alkyl is covalently bonded to the oxygen at the 3-position instead of R$_1$;
R$_3$ is hydrogen, alkyl, aryl, or aralkyl;
R$_4$ is hydrogen, alkyl, aryl, aralkyl, or —CO$_2$R$_6$ in which R$_6$ is hydrogen, alkyl, aryl, or aralkyl; and
n is 1 to 6;
or a pharmaceutically acceptable acid addition salt thereof.

Examples of compounds of formula II include those where R$_1$ is hydrogen, or those where R$_2$ is —CH$_2$OH, or —CH$_2$-O-alkyl- in which alkyl is covalently bonded to the oxygen at the 3-position instead of R$_1$, or those where R$_3$ is hydrogen, or those where R$_4$ is alkyl or hydrogen. Additional examples of compounds of formula II include those where R$_4$ is ethyl.

In still another aspect, the compounds of the invention include (2-methyl-3-hydroxy-4-hydroxymethyl-5-pyridyl) ethylphosphonate analogues. Such compounds are represented by formula III:

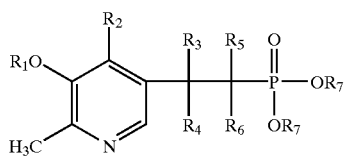

III in which
R$_1$ is hydrogen or alkyl;
R$_2$ is —CHO, —CH$_2$OH, —CH$_3$ or —CO$_2$R$_8$ in which R$_8$ is hydrogen, alkyl, or aryl; or
R$_2$ is —CH$_2$-O-alkyl- in which alkyl is covalently bonded to the oxygen at the 3-position instead of R$_1$;
R$_3$ is hydrogen and R$_4$ is hydroxy, halo, alkoxy or alkylcarbonyloxy; or
R$_3$ and R$_4$ can be taken together to form =O;
R$_5$ and R$_6$ are hydrogen; or
R$_5$ and R$_6$ are halo; and
R$_7$ is hydrogen, alkyl, aryl, aralkyl, or —CO$_2$R$_8$ in which R$_8$ is hydrogen, alkyl, aryl, or aralkyl;
or a pharmaceutically acceptable acid addition salt thereof.

Examples of compounds of formula III include those where R$_1$ is hydrogen, or those where R$_2$ is —CH$_2$OH, or —CH$_2$-O-alkyl- in which alkyl is covalently bonded to the oxygen at the 3-position instead of R$_1$, or those where R$_3$ and R$_4$ taken together form =O, or those where R$_5$ and R$_6$ are F, or those where R$_7$ is alkyl. Additional examples of compounds of formula III include those where R$_4$ is OH or CH$_3$C(O)O—, those where R$_7$ is ethyl.

In yet another aspect, the compounds of the invention include pyridoxine malonate analogues such as, for example, ((2-methyl-3-hydroxy-4-hydroxymethyl-5-pyridylmethyl)malonates). Such compounds are represented by the formula IV:

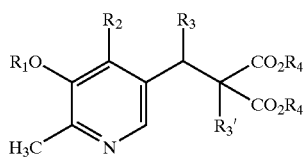

IV in which
R$_1$ is hydrogen or alkyl;
R$_2$ is —CHO, —CH$_2$OH, —CH$_3$ or —CO$_2$R$_5$ in which R$_5$ is hydrogen, alkyl, or aryl; or
R$_2$ is —CH$_2$-O-alkyl- in which alkyl is covalently bonded to the oxygen at the 3-position instead of R$_1$;
R$_3$ and R$_3$' are independently hydrogen or halo; or
R$_3$ and R$_3$' taken together constitute a second covalent bond between the carbons to which they are substituent; and
R$_4$ is hydrogen or alkyl;
or a pharmaceutically acceptable acid addition salt thereof.

Examples of compounds of formula IV include those where R$_1$ is hydrogen, or those where R$_2$ is —CH$_2$OH, or —CH$_2$-O-alkyl- in which alkyl is covalently bonded to the oxygen at the 3-position instead of R$_1$, or those where R$_3$ and R$_3$' are independently hydrogen or F, or those where R$_4$ is hydrogen or ethyl. Additional examples of compounds of formula IV include those where R$_3$ and R$_3$' taken together constitute a second covalent bond between the carbons to which they are substituent.

Pharmaceutically acceptable acid addition salts of the compounds of formulas I, II, III or IV include salts derived from nontoxic inorganic acids such as hydrochloric, nitric, phosphoric, sulfuric, hydrobromic, hydriodic, hydrofluoric, phosphorus, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., *J. Pharmaceutical Science*, 66: 1–19 (1977)).

The acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Syntheses

To prepare a compound of formula I, 3,4-isopropylidenepyridoxine-5-al is treated with a phosphonating agent, such as, a metal salt of di-tert-butyl phosphite or dibenzyl phosphite or diphenyl phosphite, to give protected alpha-hydroxyphosphonates. The protected alpha-hydroxyphosphonates can be treated with an acylating agent in an aprotic solvent, such as acetic anhydride in pyridine, or with an alkylating agent, such as methyl iodide and sodium hydride in tetrahydrofuran (THF), to give alpha-alkylcarbonyloxy or alpha-alkyloxyphosphonates esters respectively. Alternatively the protected alpha-hydroxyphosphonates can be treated with an agent to convert the hydroxyl group to a halogen, such as conversion to a fluoro group with DAST (diethylaminosulfurtrifluoride), to prepare the alpha-halophosphonate esters. The isopropylidene protecting group is removed from the fully protected alpha-substituted phosphonates by reacting them with water and an acid, such as 20% water in acetic acid, to prepare the pyridoxine-alpha-substituted phosphonate esters. The ester groups can be removed from the phosphonate groups of the pyridoxine-alpha-substituted phosphonate esters by further treating them with acid in water, such as 20% water in acetic acid, to give the corresponding phosphonic acids as can be seen in the following scheme.

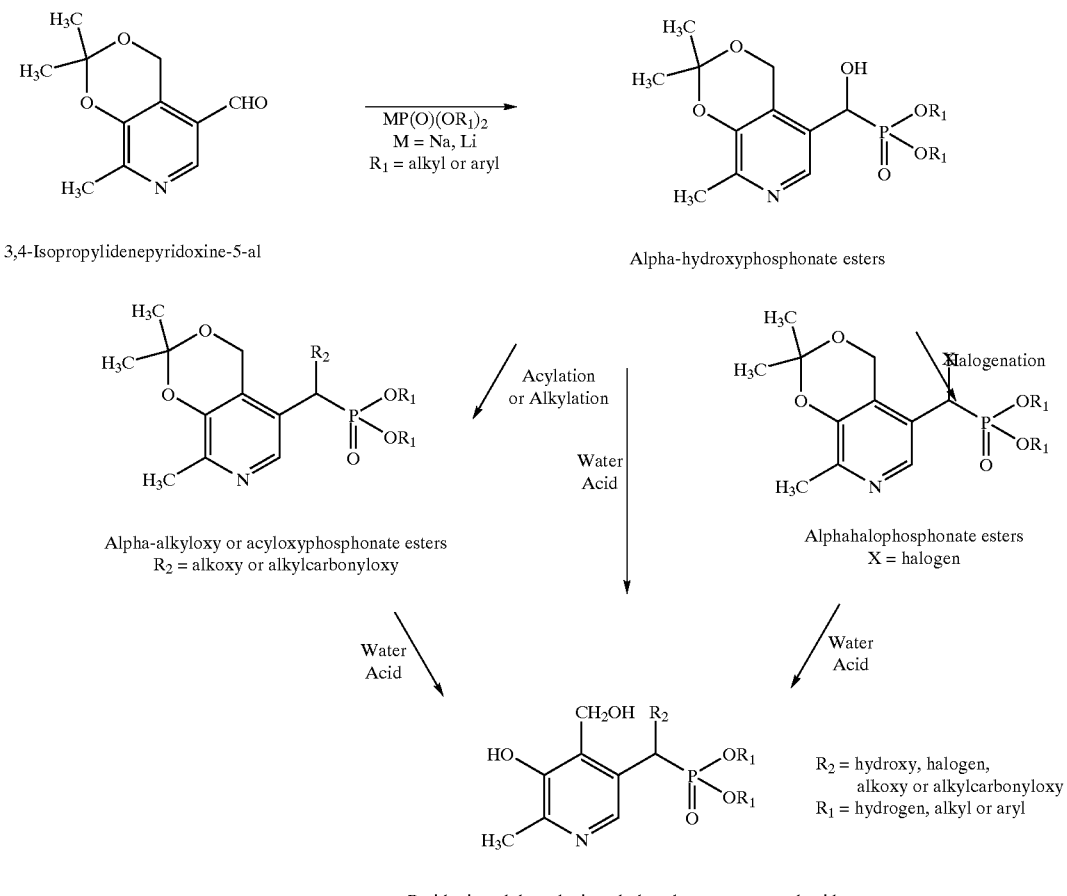

Pyridoxine-alpha-substituted phosphonate esters and acids

Alternatively, to prepare a compound of formula I, 3,4-isopropylidenepyridoxine-5-halide is treated with a phosphonating agent, such as, a metal salt of di-tert-butyl phosphite 15 or dibenzyl phosphite or diphenyl phosphite, to give protected phosphonates. The protected phosphonates are treated with a base, such as sodium hexamethyldisilazane (NaHMDS), and a halogenating agent, such as N-fluorobenzenesulfonimide (NFSi), to provide the dihalophosphonates as can be seen in the following scheme.

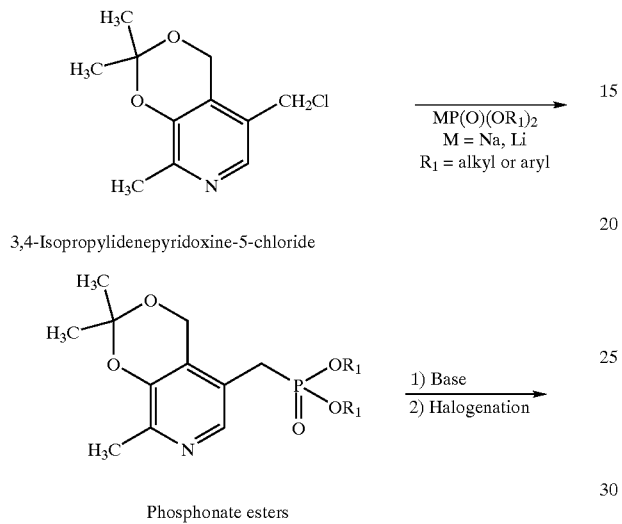

3,4-Isopropylidenepyridoxine-5-chloride

Phosphonate esters

Dihalophosphonate esters
X = halogen

Alternatively, to prepare a compound of formula 1,3,4-isopropylidenepyridoxine-5-al is treated with an amine, such as p-methoxyaniline or p-aminobiphenyl, and a phosphonating agent, such as, a metal salt of di-tert-butyl phosphite, dibenzyl phosphite or diphenyl phosphite, to give protected aminophosphonates as can be seen in the following scheme.

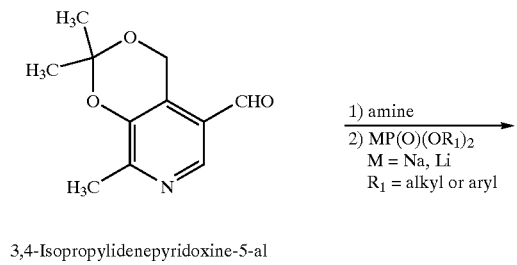

3,4-Isopropylidenepyridoxine-5-al

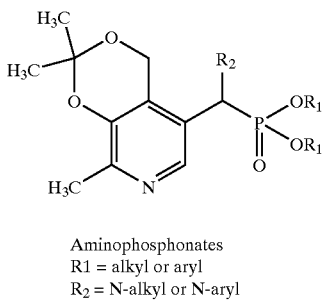

Aminophosphonates
R1 = alkyl or aryl
R2 = N-alkyl or N-aryl

To prepare a compound of formula II, 3,4-isopropylidenepyridoxine-5-amine is used as a starting material. The amine is treated with a haloalkylphosphonate diester, such as diethyl bromomethylphosphonate, to give 5'-phosphonoazaalkylpyridine diesters. Reaction of the 3,4-isopropylidene-5'-phosphonoazaalkylpyridoxine diesters with a trialkylsilyl halide, such as trimethylsilyl bromide, in an aprotic solvent, such as acetonitrile, removes the ester groups of the phosphonate diester to provide the corresponding free 3,4-isopropylidene-5'-phosphonoazaalkylpyridoxine diacid. The acetonide protecting group on the 3 and 4 position of the pyridoxine ring on the 3,4-isopropylidene-5'-phosphonoazaalkylpyridoxine diacid can be removed by reaction with acid and water, such as 20% water in acetic acid as can be seen in the following scheme.

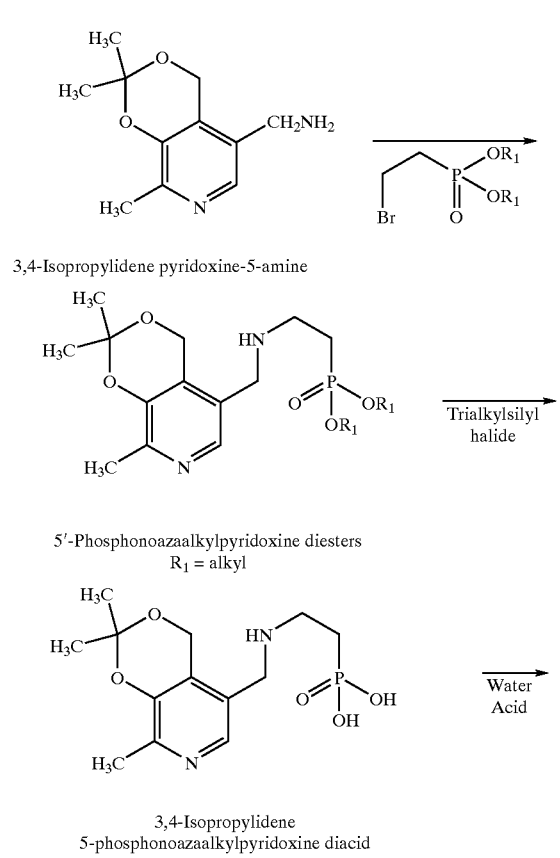

3,4-Isopropylidene pyridoxine-5-amine

5'-Phosphonoazaalkylpyridoxine diesters
$R_1$ = alkyl 3,4-Isopropylidene
5-phosphonoazaalkylpyridoxine diacid

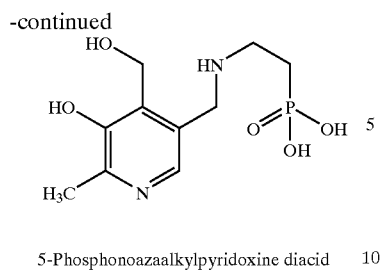

5-Phosphonoazaalkylpyridoxine diacid

To prepare a compound of formula III, 3,4-isopropylidenepyridoxine-5-al is reacted with a metal salt of a methyl, or dihalomethyl, phosphonate diester to produce 5'-phosphonoalkylpyridoxine diesters. The 5'-hydroxyl group of this product is acylated by an acylating agent, such as acetic anhydride in pyridine, to provide the corresponding O-acyl derivatives respectively, or oxidized to the keto functional group by an oxidizing agent, such as manganese dioxide. The blocking group at the 3 and 4 positions and the phosphonate ester groups of the hydroxy, alkylcarbonyloxy and keto phosphonate diesters are hydrolysed by reaction with acid and water, such as 20% water in acetic acid, to provide the corresponding phosphonate diesters, without the blocking group at the 3 and 4 position. These reactions are illustrated in the following scheme.

acid products. These reactions are illustrated in the following scheme.

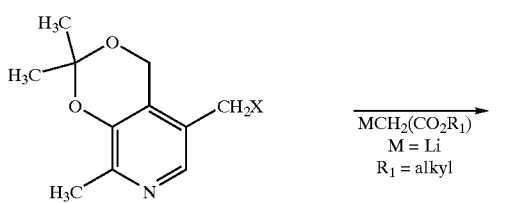

3,4-Isopropylidene-5-halide
X = halo

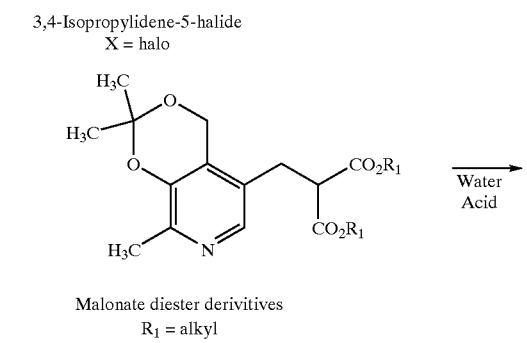

Malonate diester derivitives
$R_1$ = alkyl

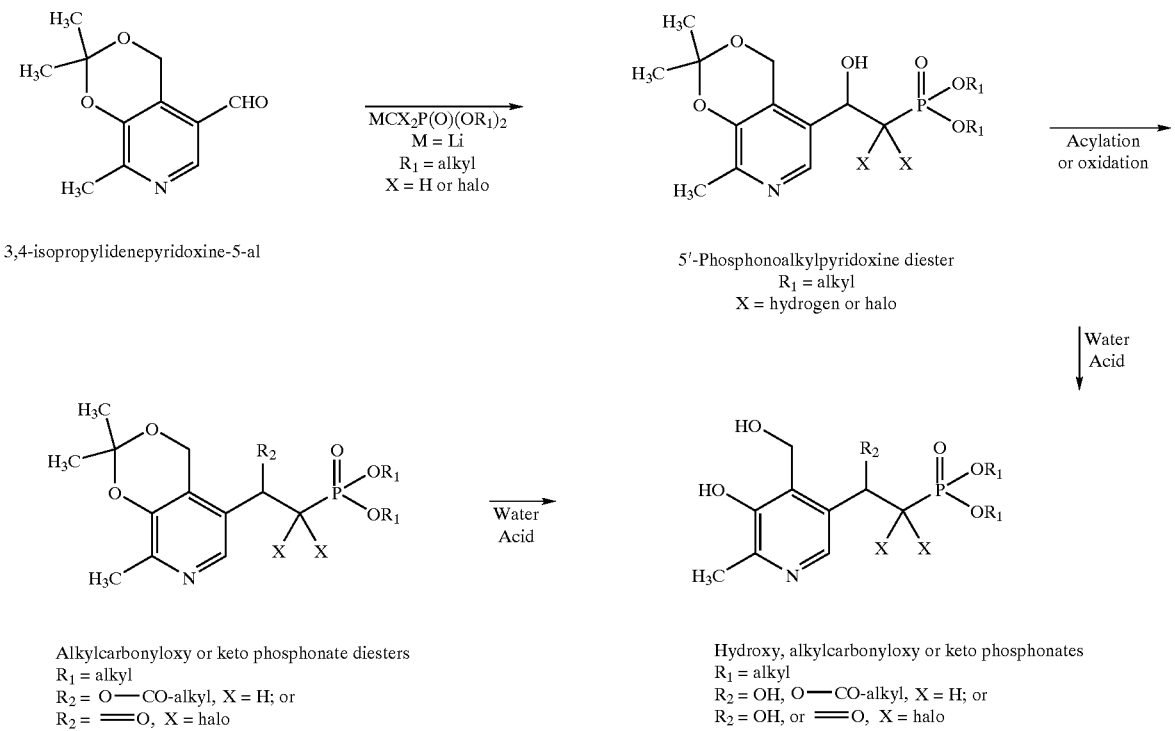

To prepare a compound of formula IV, the 3,4-isopropylidenepyridoxine-5-halide is reacted with a metal salt of a malonate diester to give the malonate diester derivative. The malonate diester derivative is hydrolysed in aqueous acid, such as 20% water in acetic acid, to remove the blocking group at the 3 and 4 position of the pyridoxine ring. The ester groups of the malonate are hydrolysed with water and base, such as sodium hydroxide in water, followed by acidification to provide the corresponding free malonic

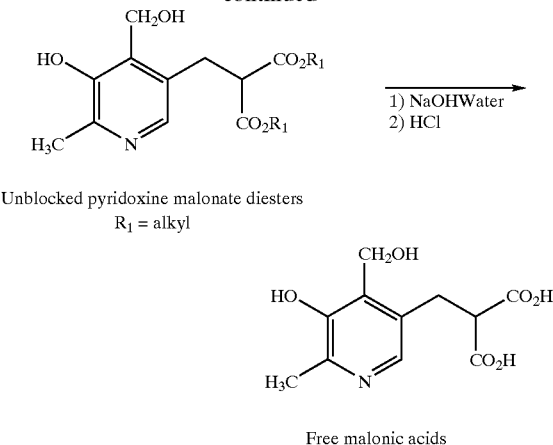

Unblocked pyridoxine malonate diesters
$R_1$ = alkyl

Free malonic acids

Alternatively, to prepare a compound of formula IV, 3,4-isopropylidenepyridoxine-5-al is reacted with a condensing agent, such as titanium tetrachloride, and a malonate diester, such as diethyl malonate, to provide a vinylene malonate diester. The vinylene malonate diester is reacted with a fluorinating agent, such as Selectfluor, to give a dihalomalonate derivative. These reactions are illustrated in the following scheme.

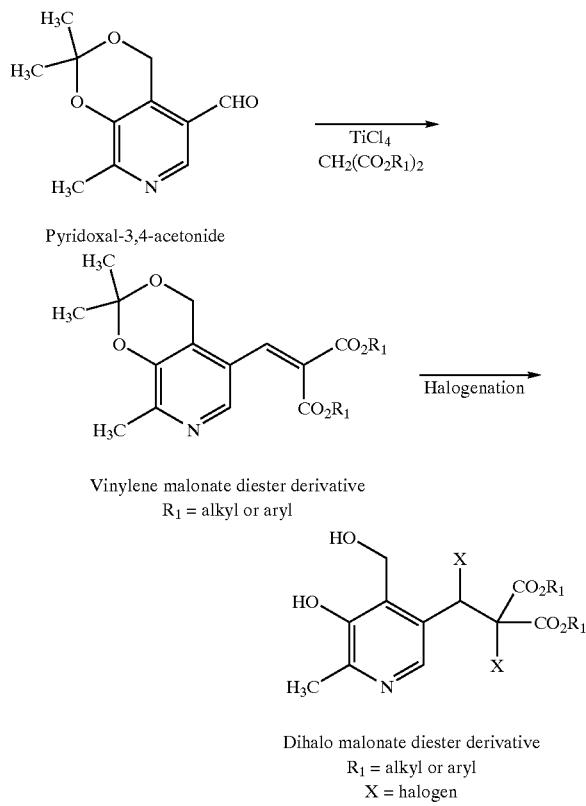

Pyridoxal-3,4-acetonide

Vinylene malonate diester derivative
$R_1$ = alkyl or aryl

Dihalo malonate diester derivative
$R_1$ = alkyl or aryl
X = halogen

One skilled in the art would recognize variations in the sequence of steps and would recognize variations in the appropriate reaction conditions from the analogous reactions shown or otherwise known that can be appropriately used in the above-described processes to make the compounds of formula I, II, III or IV herein.

The products of the reactions described herein are isolated by conventional means such as extraction, distillation, chromatography, and the like.

Methods of Use

In accordance with the present invention, the analogues can be used in the treatment of cardiovascular and related diseases; and in the treatment of diabetes mellitus and related diseases.

Cardiovascular and related diseases include, for example, hypertension, hypertrophy, congestive heart failure, heart failure subsequent to myocardial infarction, arrhythmia, myocardial ischemia, myocardial infarction, ischemia reperfusion injury, and diseases that arise from thrombotic and prothrombotic states in which the coagulation cascade is activated.

Diabetes mellitus and related diseases include, for example, hyperinsulinemia, insulin resistance, obesity, diabetes-induced hypertension, and damage to blood vessels, eyes, kidneys, nerves, autonomic nervous system, skin, connective tissue, and immune system.

"Treatment" and "treating" as used herein include preventing, inhibiting, alleviating, and healing cardiovascular and related diseases; diabetes mellitus and related diseases; or symptoms thereof. Treatment can be carried out by administering a therapeutically effective amount of a compound of the invention. A "therapeutically effective amount" as used herein includes a prophylactic amount, for example, an amount effective for preventing or protecting against cardiovascular and related diseases; diabetes mellitus and related diseases; or symptoms thereof, and amounts effective for alleviating or healing cardiovascular and related diseases; or diabetes mellitus and related diseases; or symptoms thereof.

A physician or veterinarian of ordinary skill readily determines a subject who is exhibiting symptoms of any one or more of the diseases described above. Regardless of the route of administration selected, the compounds of the present invention of formula 1, II, III or IV or a pharmaceutically acceptable acid addition salt thereof can be formulated into pharmaceutically acceptable unit dosage forms by conventional methods known to the pharmaceutical art. An effective but nontoxic quantity of the compound is employed in treatment. The compounds can be administered in enteral unit dosage forms, such as, for example, tablets, sustained-release tablets, enteric coated tablets, capsules, sustained-release capsules, enteric coated capsules, pills, powders, granules, solutions, and the like. They can also be administered parenterally, such as, for example, subcutaneously, intramuscularly, intradermally, intramammarally, intravenously, and other administrative methods known in the art.

Although it is possible for a compound of the invention to be administered alone in a unit dosage form, preferably the compound is administered in admixture as a pharmaceutical composition. A pharmaceutical composition comprises a pharmaceutically acceptable carrier and at least one compound of formula I, II, III or IV, or a pharmaceutically acceptable acid addition salt thereof. A pharmaceutically acceptable carrier includes, but is not limited to, physiological saline, ringers, phosphate-buffered saline, and other carriers known in the art. Pharmaceutical compositions can also include additives, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier and at least one compound of formula I, II, III or IV or a pharmaceutically acceptable acid addition salt thereof are known to those of skill in the art. All methods can include the step of bringing the compound of the invention in association with the carrier and additives. The formulations generally are prepared by uniformly and intimately bringing the compound of the invention into association with a liquid carrier or a finely divided solid carrier or both, and then, if necessary, shaping the product into the desired unit dosage form.

The ordinarily skilled physician or veterinarian will readily determine and prescribe the therapeutically effective amount of the compound to treat the disease for which treatment is administered. In so proceeding, the physician or veterinarian could employ relatively low dosages at first, subsequently increasing the dose until a maximum response is obtained. Typically, the particular disease, the severity of the disease, the compound to be administered, the route of administration, and the characteristics of the mammal to be treated, for example, age, sex, and weight, are considered in determining the effective amount to administer. Administering a therapeutic amount of a compound of the invention for treating cardiovascular and related diseases; diabetes mellitus and related diseases; or symptoms thereof, is in a range of 0.1–100 mg/kg of a patient's body weight, more preferably in the range of 0.5–50 mg/kg of a patient's body weight, per daily dose. The compound can be administered for periods of short and long duration. Although some individual situations can warrant to the contrary, short-term administration, for example, 30 days or less, of doses larger than 25 mg/kg of a patient's body weight is preferred to long-term administration. When long-term administration, for example, months or years, is required, the suggested dose should not exceed 25 mg/kg of a patient's body weight.

A therapeutically effective amount of a compound for treating the above-identified diseases or symptoms thereof can be administered prior to, concurrently with, or after the onset of the disease or symptom.

The compound also can be administered to treat cardiovascular and related diseases, for example, hypertrophy, hypertension, congestive heart failure, heart failure subsequent to myocardial infarction, myocardial ischemia, ischemia reperfusion injury, arrhythmia, or myocardial infarction. Preferably, the cardiovascular disease treated is hypertrophy or congestive heart failure. Still preferably, the cardiovascular disease treated is arrhythmia. Also preferably, the cardiovascular disease treated is ischemia reperfusion injury.

The compound can also be administered to treat cardiovascular diseases and other diseases that arise from thrombotic and prothrombotic states in which the coagulation cascade is activated, such as, for example, deep vein thrombosis, disseminated intravascular coagulopathy, Kasabach-Merritt syndrome, pulmonary embolism, myocardial infarction, stroke, thromboembolic complications of surgery, and peripheral arterial occlusion. A compound of the invention may also be useful in the treatment of adult respiratory distress syndrome, septic shock, septicemia, or inflammatory responses, such as edema and acute or chronic atherosclerosis, because thrombin has been shown to activate a large number of cells outside of the coagulation process, such as, for example, neutrophils, fibroblasts, endothelial cells, and smooth muscle cells.

Moreover, the compound can be administered concurrently with compounds that are already known to be suitable for treating the above-identified diseases. For example, methods of the invention include concurrently administering at least one compound of formula I, II, III or IV a pharmaceutically acceptable acid addition salt thereof, or a mixture thereof with a therapeutic cardiovascular compound to treat hypertrophy, hypertension, congestive heart failure, heart failure subsequent to myocardial infarction, myocardial ischemia, ischemia reperfusion injury, arrhythmia, or myocardial infarction. Preferably the cardiovascular disease treated is hypertrophy or congestive heart failure. Still preferably, the cardiovascular disease treated is arrhythmia. Also preferably, the cardiovascular disease treated is ischemia reperfusion injury.

Therapeutic cardiovascular compounds that can be concurrently administered with at least one compound of the invention include an angiotensin converting enzyme inhibitor, an angiotensin II receptor antagonist, a calcium channel blocker, an antithrombolytic agent, a β-adrenergic receptor antagonist, a vasodilator, a diuretic, an α-adrenergic receptor antagonist, an antioxidant, and a mixture thereof. A compound of the invention also can be concurrently administered with PPADS (pyridoxal phosphate-6-azophenyl-2', 4'-disulphonic acid), also a therapeutic cardiovascular compound, or with PPADS and another known therapeutic cardiovascular compound as already described.

Preferably a therapeutic cardiovascular compound, which is concurrently administered with at least one compound of formula I, II, III or IV, a pharmaceutically acceptable acid addition salt thereof, or a mixture thereof, is an angiotensin converting enzyme inhibitor, an angiotensin II receptor antagonist, or a diuretic. Still preferably, the therapeutic cardiovascular compound is an α-adrenergic receptor antagonist. Also preferably, the therapeutic cardiovascular compound is a calcium channel blocker.

These therapeutic cardiovascular compounds are generally used to treat cardiovascular and related diseases as well as symptoms thereof A skilled physician or veterinarian readily determines a subject who is exhibiting symptoms of any one or more of the diseases described above and makes the determination about which compound is generally suitable for treating specific cardiovascular conditions and symptoms.

For example, myocardial ischemia can be treated by the administration of, for example, angiotensin converting enzyme inhibitor, an angiotensin II receptor antagonist, a calcium channel blocker, an antithrombolytic agent, a β-adrenergic receptor antagonist, a diuretic, an α-adrenergic receptor antagonist, or a mixture thereof. In some instances, congestive heart failure can be treated by the administration of, for example, angiotensin converting enzyme inhibitor, an angiotensin II receptor antagonist, a calcium channel blocker, a vasodilator, a diuretic, or a mixture thereof.

Myocardial infarction can be treated by the administration of, for example, angiotensin converting enzyme inhibitor, a calcium channel blocker, an antithrombolytic agent, a β-adrenergic receptor antagonist, a diuretic, an α-adrenergic receptor antagonist, or a mixture thereof.

Hypertension can be treated by the administration of, for example, angiotensin converting enzyme inhibitor, a calcium channel blocker, a β-adrenergic receptor antagonist, a vasodilator, a diuretic, an α-adrenergic receptor antagonist, or a mixture thereof.

Moreover, arrhythmia can be treated by the administration of, for example, a calcium channel blocker, a β-adrenergic receptor antagonist, or a mixture thereof.

Antithrombolytic agents are used for reducing or removing blood clots from arteries.

Hypertrophy can be treated by the administration of, for example, an angiotensin converting enzyme inhibitor, an angiotensin II receptor antagonist, a calcium channel blocker, or a mixture thereof.

Ischemia reperfusion injury can be treated by the administration of, for example, an angiotensin converting enzyme inhibitor, an angiotensin II receptor antagonist, a calcium channel blocker, or a mixture thereof.

Known angiotensin converting enzyme inhibitors include, for example, captopril, enalapril, lisinopril, benazapril, fosinopril, quinapril, ramipril, spirapril, imidapril, and moexipril.

Examples of known angiotensin II receptor antagonists include both angiotensin I receptor subtype antagonists and angiotensin II receptor subtype antagonists. Suitable antiotensin II receptor antagonists include losartan and valsartan.

Suitable calcium channel blockers include, for example, verapamil, diltiazem, nicardipine, nifedipine, amlodipine, felodipine, nimodipine, and bepridil.

Antithrombolytic agents known in the art include anti-platelet agents, aspirin, and heparin.

Examples of known β-adrenergic receptor antagonists include atenolol, propranolol, timolol, and metoprolol.

Suitable vasodilators include, for example, hydralazine, nitroglycerin, and isosorbide dinitrate.

Suitable diuretics include, for example, furosemide, diuril, amiloride, and hydrodiuril.

Suitable α-adrenergic receptor antagonists include, for example, prazosin, doxazocin, and labetalol.

Suitable antioxidants include vitamin E, vitamin C, and isoflavones.

At least one compound of formula I, II, III or IV, a pharmaceutically acceptable acid addition salt thereof, or a mixture thereof and a therapeutic cardiovascular compound can be administered concurrently. "Concurrent administration" and "concurrently administering" as used herein includes administering a compound of the invention and a therapeutic cardiovascular compound in admixture, such as, for example, in a pharmaceutical composition or in solution, or as separate compounds, such as, for example, separate pharmaceutical compositions or solutions administered consecutively, simultaneously, or at different times but not so distant in time such that the compound of the invention and the therapeutic cardiovascular compound cannot interact and a lower dosage amount of the active ingredient cannot be administered.

At least one compound of formula I, II, III or IV, a pharmaceutically acceptable acid addition salt thereof, or a mixture thereof also can be administered to treat diabetes mellitus and related diseases. Preferably the disease treated is type I diabetes, type II diabetes, or obesity. Also preferably, the disease treated is damage to blood vessels, eyes, kidneys, nerves, autonomic nervous system, skin, connective tissue, or immune system. Still preferably, the disease treated is insulin resistance or hyperinsulinemia. And preferably, the disease treated is diabetes-induced hypertension.

The method of the invention also includes concurrently administering at least one compound of formula I, II, III or IV, a pharmaceutically acceptable acid addition salt thereof, or a mixture thereof with insulin and/or a hypoglycemic compound to treat diabetes mellitus and related diseases. The compound can be administered concurrently with insulin and/or a hypoglycemic compound to treat type I diabetes, type II diabetes, or obesity. Preferably the compound can be administered concurrently with insulin and/or hypoglycemic compound to treat damage to blood vessels, eyes, kidneys, nerves, autonomic nervous system, skin, connective tissue, or immune system. Still preferably, the compound can be administered concurrently with insulin and/or hypoglycemic compound to treat insulin resistance or hyperinsulinemia. Also preferably, the compound can be administered concurrently with insulin and/or hypoglycemic compound to treat diabetes-induced hypertension.

A compound typically can be administered concurrently with insulin to treat type I diabetes, type II diabetes, and related conditions and symptoms. For type II diabetes, insulin resistance, hyperinsulinemia, diabetes-induced hypertension, obesity, or damage to blood vessels, eyes, kidneys, nerves, autonomic nervous system, skin, connective tissue, or immune system, a compound can be administered concurrently with a hypoglycemic compound instead of insulin. Alternatively, a compound can be administered concurrently with insulin and a hypoglycemic compound to treat type II diabetes, insulin resistance, hyperinsulinemia, diabetes-induced hypertension, obesity, or damage to blood vessels, eyes, kidneys, nerves, autonomic nervous system, skin, connective tissue, or immune system.

"Concurrent administration" and "concurrently administering" as used herein includes administering at least one compound of formula I, II, III or IV, a pharmaceutically acceptable acid addition salt thereof, or a mixture thereof and insulin and/or a hypoglycemic compound in admixture, such as, for example, in a pharmaceutical composition, or as separate compounds, such as, for example, separate pharmaceutical compositions administered consecutively, simultaneously, or at different times. Preferably, if the compound and insulin and/or hypoglycemic compound are administered separately, they are not administered so distant in time from each other that the compound and the insulin and/or hypoglycemic compound cannot interact and a lower dosage amount of insulin and/or hypoglycemic compound cannot be administered.

Suitable hypoglycemic compounds include, for example, metformin, acarbose, acetohexamide, glimepiride, tolazamide, glipizide, glyburide, tolbutamide, chlorpropamide, and a mixture thereof. Preferably the hypoglycemic compound is tolbutamide.

This invention will be further characterized by the following examples. These examples are not meant to limit the scope of the invention, which has been fully set forth in the foregoing description. Variations within the scope of the invention will be apparent to those skilled in the art.

EXAMPLES

All reagents used in the following Examples can be purchased from Aldrich Chemical Company (Milwaukee, Wis. or Allentown, Pa.).

Example 1

Synthesis of Di-t-butyl ($\alpha^4$,3-O-isopropylidene-3-hydroxy-4-hydroxymethyl-2-methyl-5-pyridyl) hydroxymethylphosphonate Di-tert-butyl phosphite (16.3 g, 84 mmol) was added to a solution of NaH (3.49 g, 60%, 87.2 mmol) in THF (60 mL) under nitrogen at 0° C. The temperature of the resulting solution was raised to room temperature and the solution stirred for 15 min, then cooled to 0° C. again. To this solution, ($\alpha^4$,3-O-isopropylidene-3-hydroxy-4-hydroxymethyl-2-methyl-5-pyridyl)methanal (Kortynk et al., J. Org. Chem., 29, 574–579 (1964)) (11.41 g, 55.05 mmol) in THF (30 mL) was slowly added then the temperature raised to room temperature again and stirring continued for 2 h. The reaction was quenched by adding saturated NaHCO$_3$ (40 ml), and diluted with diethyl ether (200 mL). The ether layer was separated, washed with saturated aqueous NaHCO$_3$ (40 ml, 5%), then saturated brine (3×20 mL). The ether layer was dried (MgSO$_4$), filtered and evaporated to give crude product as a colorless solid. This solid was washed with hexane to remove the oil (from the NaH) and unreacted phosphite. The solid was recrystallized from a mixture of diethyl ether:hexane:ethyl acetate (230 mL: 70 mL: 15 mL). The colorless crystal (17.9 g, 81%) were filtered and washed with hexane.

$^1$H NMR (CDCl$_3$): 1.42 (9H, d), 1.46 (9H, d), 1.51 (6H, d), 2.38 (3H, s), 4.70 (1H, d), 4.89–5.13 (2H, m), 8.11 (1H, s).

$^{31}$P NMR (H-decoupled, CDCl$_3$): 13.43 (s).

This structure can be represented by formula V:

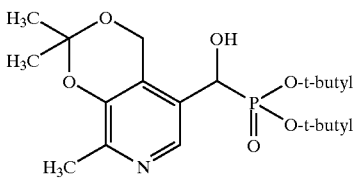

V

Example 2

Synthesis of Dibenzyl ($\alpha^4$,3-O-isopropylidene-3-hydroxy-4-hydroxymethyl-2-methyl-5-pyridyl) hydroxymethylphosphonate Dibenzyl phosphite (1.89 g, 9.62 mmol) was mixed with the ($\alpha^4$,3-O-isopropylidene-3-hydroxy-4-hydroxymethyl-2-methyl-5-pyridyl)methanal (Kortynk et al., J. Org. Chem., 29, 574–579 (1964)) (1.00 g, 4.81 mmol) and stirred at room temperature for an hour. To this thick syrup was added activated basic alumina (1 g). The reaction mixture was then stirred at 80° C. for one hour. The reaction mixture was diluted with dichloromethane (50 mL), and filtered through Celite to remove alumina. The dichloromethane solution was washed with saturated, aqueous NaHCO$_3$ (20 mL), then saturated brine (3×10 mL). The dichloromethane layer was dried (MgSO$_4$), filtered and evaporated to give crude product as a colorless solid. The crude product was purified by silica gel column chromatography, using ether: hexanes (1:2) as eluent to give 1.3 g (58%).

$^1$H NMR (CDCl$_3$): 1.30 (3H, s), 1.45 (3H, s), 2.30 (3H, s), 4.86–4.99 (7H, s), 7.18–8.07 (10H, s), 8.08 (1H, s).

This structure can be represented by formula VI:

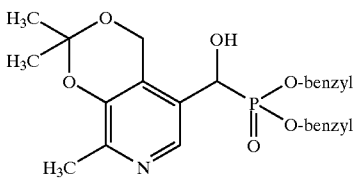

VI

Example 3

Synthesis of (3-hydroxy-4-hydroxymethyl-2-methyl-5-pyridyl)hydroxymethyl Phosphonic Acid The product of Example I above, of formula V, (10 g, 24.9 mmol) was dissolved in acetic acid (80% in water, 100 ml) and heated at 60° C. for 1 d. Colorless precipitate was formed, however, the reaction was not complete. Another 50 ml of 80% acetic acid in water was added to the mixture and the mixture stirred at 60° C. for another day. The solid was filtered off, washed with cold water, then methanol and dried to give a colorless solid (4.78 g, 77%).

$^1$H NMR (D$_2$O): 2.47 (3H, s), 4.75–4.79 (2H, m), 5.15–5.19 (1H, d), 7.82 (1H, s).

$^{31}$P NMR (H-decoupled D$_2$O): 14.87 (s).

This structure can be represented by formula VII:

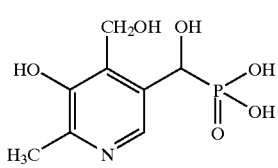

VII

Example 4

Synthesis of Dibenzyl ($\alpha^4$,3-O-isopropylidene-3-hydroxy-4-hydroxymethyl-2-methyl-5-pyridyl) fluoromethylphosphonate The protected alpha-hydroxy phosphonate from Example 2 above of structure VI (1.0 g, 2.49 mmol) was dissolved in dichloromethane (10 mL), and the solution cooled to −78° C. To this solution was added diethylaminosulfurtrifluoride (DAST) (0.8 g, 4.98 mmol). The reaction was stirred at −78° C. under nitrogen for 20 minutes then allowed to stand at room temperature overnight. The reaction mixture was diluted with dichloromethane (50 ml), and washed with saturated, aqueous NaHCO$_3$ (125 mL). The dichloromethane layer was dried (MgSO$_4$), filtered and evaporated to give crude fluorophosphonate as a yellow solid. The crude product was purified by silica gel column chromatography, using ethyl acetate: hexanes (2:1) as the eluent to give 600 mg (60%).

$^1$H NMR (CDCl$_3$): 1.42 (3H, s), 1.52 (3H, s), 2.40 (3H, s), 4.91–4.97 (6H, m), 5.46–5.61 (1H, dd), 7.23–7.34 (10H, m), 8.01 (1H, s).

$^{31}$P NMR (H-decoupled, F-coupled, CDCl$_3$): 16.36–16.08 (d).

This structure can be represented by formula VIII:

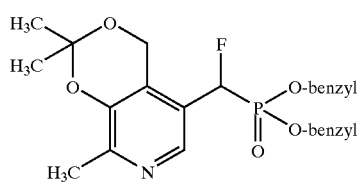

VIII

Example 5

Synthesis of Di-t-butyl ($\alpha^4$,3-O-isopropylidene-3-hydroxy-4-hydroxymethyl-2-methyl-5-pyridyl) fluoromethylphosphonate The protected alpha-hydroxy phosphonate from Example 1 of structure V (3 g, 7.55 mmol) was dissolved in dichloromethane (30 mL), and the solution cooled to −78° C. To this solution was added diethylaminosulfurtrifluoride (DAST) (1.22 g, 7.57 mmol). The reaction was stirred at −78° C. under nitrogen for 5 minutes, quenched by addition of saturated, aqueous NaHCO$_3$ (2 mL) then allowed to warm room temperature. The reaction mixture was diluted with dichloromethane (50 ml), and washed with saturated, aqueous NaHCO$_3$ (2×20 mL). The dichloromethane layer was dried (MgSO$_4$), filtered and evaporated to give crude fluorophosphonate. The crude product was purified by silica gel column chromatography, using ethyl acetate: hexanes (1:1) as the eluent to give 350 mg (12%).

$^1$H NMR (CDCl$_3$): 1.44 (9H, s), 1.46 (9H, s), 1.52 (3H, s), 1.56 (3H, s), 2.41 (3H, s), 4.98–5.14 (2H, m), 5.32–5.52 (1H, dd), 8.03 (1H, s).

$^{31}$P NMR (H-decoupled, F-coupled, CDCl$_3$): 6.53, 7.24.

$^{19}$F NMR (H-decoupled, CDCl$_3$): −202.6, −203.0

This structure can be represented by formula IX:

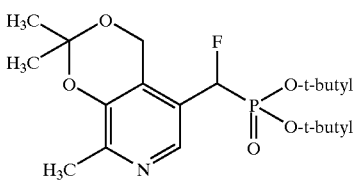

IX

Example 6

Synthesis of Di-t-butyl (3-hydroxy-4-hydroxymethyl-2-methyl-5-pyridyl)fluoromethyl Phosphonate The protected di-t-butyl alpha-fluoro phosphonate from Example 5 of structure IX (3.2 g 7.8 mmol) was dissolved in acetic acid (80% in water, 50 ml) and heated at 60° C. for 24 hours. The pale yellow solid was filtered off, washed with cold water and methanol, and then dried to give a creamy solid (2.21 g, 70%).

$^1$H NMR (CDCl$_3$): 1.41 (9H, s), 1.44 (9H, s), 1.49 (3H, s), 1.51 (3H, s), 2.42 (3H, s), 4.99–5.07 (2H, m), 5.33–5.51 (1H, d,d), 8.04 (1H, s).

$^{31}$P NMR (H-decoupled, F-Coupled, CDCl$_3$): 7.10–780 (d).

$^{19}$F NMR (H, P-Coupled, CDCl$_3$): −203.07 to −202.61 (dd).

This structure can be represented by formula X:

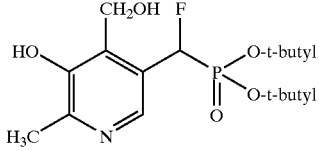

X

Example 7

Synthesis of (3-hydroxy-4-hydroxymethyl-2-methyl-5-pyridyl)fluoromethyl Phosphonic Acid The protected di-t-butyl alpha-fluoro phosphonate from Example 5 of structure IX (200 mg, 0.5 mmol) was dissolved in acetic acid (80% in water, 15 ml) and heated at 75° C. for 24 hours. The solvent was removed by evaporation on a rotary evaporator using toluene to codistill the water. The crude product (183 mg) was purified by column chromatography on silica using chloroform:methanol:water (65:35:2) as eluent to give 60 mg (55%).

$^1$H NMR (D$_2$O): 2.46 (3H, bs), 4.65–4.90 (2H, dd), 5.81–6.01 (1H, dd), 7.74 (1H, bs).

$^{31}$P NMR (H-decoupled, F-Coupled, CDCl$_3$): 9.3 (d).

$^{19}$F NMR (H, P-Coupled, CDCl$_3$): −197 to −196 (dd).

This structure can be represented by formula XI:

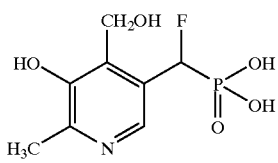

XI

Example 8

Synthesis of Di-t-butyl ($\alpha^4$,3-O-isopropylidene-3-hydroxy-4-hydroxymethyl-2-methyl-5-pyridyl) acetoxymethylphosphonate The product of Example 1 above, of formula V (1.0 g, 2.49 mmol) was dissolved in dichloromethane (20 mL), the solution cooled to −5° C., and pyridine (2 mL) added, followed by acetic anhydride (1 mL). The reaction temperature was slowly allowed to reach room temperature. After one hour, the reaction was quenched by adding dilute aqueous hydrochloric acid (10%, 75 mL), and then diluted with dichloromethane (25 mL). Afterm separation of the aqueous layer the methylene chloride layer washed with saturated NaHCO$_3$ (2×20 mL). The dichloromethane layer was dried (MgSO$_4$), filtered and evaporated to give crude alpha acetoxy phosphonate as a colorless solid. The crude product was purified by silica gel column chromatography, using ethyl acetate: hexanes (2:1) as the eluent to give the product in good yield.

$^1$H NMR(CDCl$_3$): 1.31 (9H, d), 1.36 (9H, d), 1.49 (6H, d), 2.1 (3H s), 2.38 (3H, s), 5.04 (2H, d), 5.72–5.76 (1H, d), 8.11 (1H, s).

$^{31}$P NMR (H-decoupled, CDCl$_3$): 13.43 (s).

This structure can be represented by formula XII:

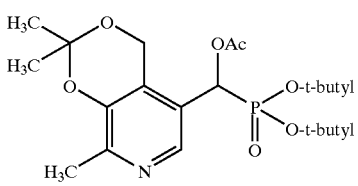

XII

Example 9

Synthesis of Di-t-butyl ($\alpha^4$,3-O-isopropylidene-3-hydroxy-4-hydroxymethyl-2-methyl-5-pyridyl) methoxymethylphosphonate The product of Example 1 above, of formula V (300 mg, 0.75 mmol) was dissolved in 15 ml of THF and reaction vessel was purged with N$_2$ gas. Sodium hydride (21 mg, 0.9 mmol) was added, and the solution stirred for 5 minutes before cooling to 0° C. Methyl iodide (160 mg, 1.1 mmol) was then injected and reaction vessel was gradually allowed to reach room temperature. TLC (ethyl acetate) indicated that the reaction was complete in 3 hours. The soution was diluted with methylene chloride (250 mL), washed with dilute, aqueous HCL (10%, 100 mL), then saturated, aqueous NaHCO$_3$, dried (MgSO$_4$) and evaporated. The crude product was chromatographed on silica gel using ethyl acetate/hexanes (1:1) as the eluent to give 132 mg (32%).

$^1$H NMR (CDCl$_3$): 1.41 (18H, s), 1.51 (3H, s), 1.54 (3H, s), 2.40 (3H, s), 3.33 (3H, s), 4.20–4.26 (1H, d), 5.05 (2H, bs), 8.01 (1H, s).

$^{31}$P NMR (H-decoupled, CDCl$_3$): 10.88 (s).

This structure can be represented by formula XIII:

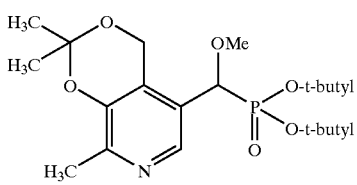

XIII

Example 10

Synthesis of (3-hydroxy-4-hydroxymethyl-2-methyl-5-pyridyl)acetoxymethyl Phosphonic Acid The product of Example 8 above, of formula XII, (50 mg, 0.11 mmol) was added to acetic acid (80% in water) and stirred for 24 hours at 60° C. The solvent was removed by evaporation on a rotary evaporator using toluene to codistill the water. The crude product was purified by chromatography on silica gel column using CH$_2$Cl$_2$/MeOH/H$_2$O (65:35:4) as eluent to give 22.8 mg (76%).

$^1$H NMR (D$_2$O): 2.23 (3H, s), 2.51 (3H, s), 4.6–5.1 (2H, m), 6.1 (1H, d), 7.85 (1H, s).

This structure can be represented by formula XIV:

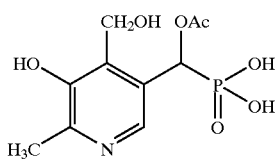

XIV

Example 11

Synthesis of (3-hydroxy-4-hydroxymethyl-2-methyl-5-pyridyl)methoxymethyl Phosphonic Acid The product of Example 9 above, of formula XIII (132 mg, 0.32 mmol) was dissolved in acetic acid (80% in water, 25 mL) and stirred at 60° C. for 24 hours. The solvent was removed by evaporation on a rotary evaporator using toluene to codistill the water. The crude product was purified by chromatography on silica gel column using CH$_2$Cl$_2$/MeOH/H$_2$O (65:35:4) as eluent to give the product in good yield.

$^1$H NMR (D$_2$O): 2.52 (3H, s), 3.32 (3H, s), 4.47–4.88 (2H, m), 7.87 (1H, s).

$^{31}$P NMR (H-decoupled, D$_2$O): 13.31 (s)

This structure can be represented by formula XV:

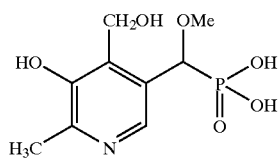

XV

Example 12

Synthesis of Dibenzyl ($\alpha^4$,3-O-isopropylidene-3-hydroxy-4-hydroxymethyl-2-methyl-5-pyridyl)difluoromethylphosphonate To a solution of dibenzyl ($\alpha^4$,3-O-isopropylidene-3-hydroxy-4-hydroxymethyl-2-methyl-5-pyridyl)methylphosphonate (115 mg, 0.253 mmol) in THF (10 mL) was added NaHMDS (1 M, 0.56 mL, 0.56 mmol). The reaction mixture was cooled to -78° C. After 15 minutes, NFSi (237 mg, 0.75 mmol) was added to the reaction mixture. The temperature of the reaction mixture was slowly warmed to -20° C. The solution was diluted with Et$_2$O, washed with saturated NaHCO$_3$, water and brine, dried (MgSO$_4$) and evaporated. The crude product was chromatographed on silica using ethyl acetate:hexanes (2:1) as eluent to give the dibenzyl ($\alpha^4$,3-O-isopropylidene-3-hydroxy-4-hydroxymethyl-2-methyl-5-pyridyl)difluoromethylphosphonate in good yields.

$^1$H NMR (CDCl$_3$) 1.53 (s, 6H), 2.45 (d, 3H), 5.34 (d, 2H), 7.09–7.39 (m, 14H), 8.29 (s,1H).

$^{31}$p NMR (CDCl$_3$) -2.15 (t).

$^{19}$F NMR (CDCl$_3$) -105.7 (d).

This structure can be represented by formula XVI:

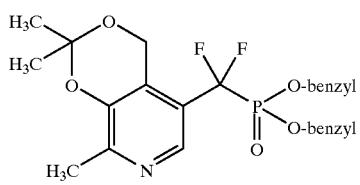

XVI

Example 13

Synthesis of Di-t-butyl ($\alpha^4$,3-O-isopropylidene-3-hydroxy-4-hydroxymethyl-2-methyl-5-pyridyl)(4-biphenylamino)methylphosphonate The ($\alpha^4$,3-O-isopropylidene-3-hydroxy-4-hydroxymethyl-2-methyl-5-pyridyl)methanal (Kortynk et al., J. Org. Chem., 29, 574–579 (1964)) (424 mg, 2.19 mmol) and 4-aminobiphenyl (360 mg, 2.12 mmol) was refluxed in benzene (20 mL) under nitrogen, using a Dean-Stark trap to remove water, for 15 hours. The crude reaction mixture was evaporated, dissolved in THF (20 mL) and added to a flask containing di-t-butyl phosphite (955 mg, 5.12 mmol) in THF (20 mL) and NaH (270 mg, 57% in oil, 6.41 mmol) and stirred at 0° C. for two hours. The solution was diluted with Et$_2$O, washed with saturated, aqueous NaHCO$_3$ (40 mL), brine (20 mL), dried (MgSO$_4$) and evaporated. The crude product was chromatographed on silica gel using hexane:diethyl ether (2:1) to give di-t-butyl ($\alpha^4$,3-O-isopropylidene-3-hydroxy-4-hydroxymethyl-2-methyl-5-pyridyl)(4-biphenylamino)methylphosphonate in modest yields.

$^1$H NMR (CDCl$_3$) 8.40 (1H, d,), 7.50–7.41 (2H, m), 7.40–7.30 (4H, m), 7.28–7.10 (1H, m), 6.54 (1H, d), 5.24 (1H, dd,), 5.07 (1H, dd,), 4.65 (1H, dd,), 4.44 (1H, dd,), 2.40 (3H, d), 1.58 (3H, s), 1.49 (3H, s), 1.43 (9H, s), 1.41 (9H, s).

$^{31}$P NMR (H-decoupled, CDCl$_3$): 13.1 (s).

This structure can be represented by formula XVII:

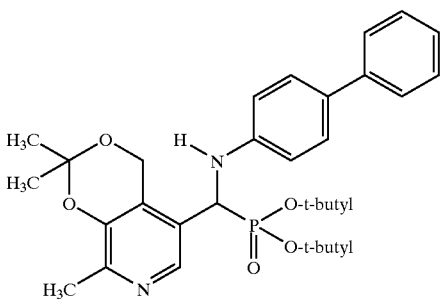

XVII

Example 14

Synthesis of Di-t-butyl ($\alpha^4$,3-O-isopropylidene-3-hydroxy-4-hydroxymethyl-2-methyl-5-pyridyl)(4-methoxyphenylamino)methylphosphonate ($\alpha^4$,3-O-Isopropylidene-3-hydroxy-4-hydroxymethyl-2-methyl-5-pyridyl)methanal (Kortynk et al., J. Org. Chem., 29, 574–579 (1964)) (2.5 g, 12.1 mmol) and 4-aminoanisole (1.41 g, 11.4 mmol) was refluxed in benzene (100 mL) under nitrogen, using a Dean-Stark trap to remove water, for 15 hours. The reaction mixture was evaporated to give 3.02 g of crude imine. The crude imine (370 mg,-1.19 mmol) was dissolved in THF (20 mL) and added to a flask containing di-t-butyl phosphite (955 mg, 5.1 mmol) in THF (20 mL) and NaH (208 mg, 57% in oil, 4.94 mmol) and stirred at 0° C. for two hours and at room temperature for 24 hours. The solution was diluted with Et$_2$O, washed with saturated, aqueous NaHCO$_3$ (40 mL), brine (40 mL), dried (MgSO$_4$) and evaporated. The crude product was chromatographed on silica gel using hexane:diethyl ether (2:1) to give di-t-butyl ($\alpha^4$,3-O-isopropylidene-3-hydroxy-4-hydroxymethyl-2-methyl-5-pyridyl)(4-methoxyphenylamino) methylphosphonate in modest yields.

$^1$H NMR (CDCl$_3$) 8.09 (1H, d), 6.70–6.60 (2H, m), 6.47–6.36 (2H, m), 5.18 (1H, dd), 4.98 (1H, dd), 4.36–4.20 (2H, m), 3.65 (3H, s), 2.35 (3H, s), 1.54 (3H, s), 1.45 (3H, s), 1.39 (9H, s), 1.38 (9H, s).

$^{31}$P NMR (decoupled, CDCl$_3$): δ 13.5 ppm.

This structure can be represented by formula XVIII:

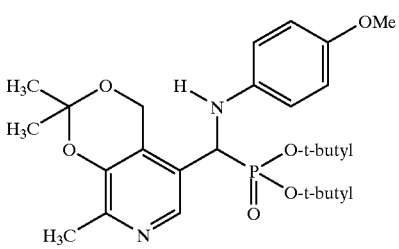

XVIII

Example 15

Synthesis of Di-t-butyl ($\alpha^4$,3-O-isopropylidene-3-hydroxy-4-hydroxymethyl-2-methyl-5-pyridyl)-3-azabutylphosphonate ($\alpha^4$,3-O-Isopropylidene-3-hydroxy-4-hydroxymethyl-2-methyl-5-pyridyl)methylbromide (Imperalli et al, J. Org. Chem., 60, 1891–1894 (1995)) (1.08 g. 4.0 mmol) in anhydrous DMF (20 ml) was treated with sodium azide (260 mg, 4.0 mmol) at room temperature. After one hour stirring at room temperature, the solution was extracted with diethyl ether (5×20 mL). The combined extracts were washed with water (10 mL), and brine (10 mL) and dried (MgSO$_4$). The solvent was evaporated and the crude product was purified by chromatography on silica gel using ethyl ether: hexanes (2:1) as eluent to give the azide as a colorless liquid (552 mg, 60%).

$^1$H NMR (CDCl$_3$, TMS) 1.57 (s, 6H), 2.42 (s, 3H), 4.23 (s, 2H), 4.86 (s, 2H), 7.96 (s, 1H). The purified azide (100 mg, 0.4 mmol) was dissolved in 95% ethanol and hydrogenated at 1 atm in presence of Lindlar catalyst (50 mg) for one hour. The catalyst was removed by filtration (Celite), and the solvent removed to give the crude amine. Purification by chromatography on silica gel using CH$_2$Cl$_2$:MeOH (5:1) as eluent gave the product (80 mg, 82%) $^1$HNMR (CD$_2$Cl$_2$) 1.53 (s, 6H), 2.34 (s, 3H), 3.72 (s, 2H), 4.91 (s, 2H), 5.31 (s, 2H), 7.93 (s, 1H).

The ($\alpha^4$,3-O-Isopropylidene-3-hydroxy-4-hydroxymethyl-2-methyl-5-pyridyl)methylamine, from above, (416 mg, 2 mmol) was heated in saturated, aqueous sodium bicarbonate solution (10 mL) to 95° C., followed by slow addition of diethyl 2-bromoethylphosphonate (0.09 mL, 0.5 mmol) and the reaction stirred at 95° C. overnight. The solution is evaporated using toluene to codistill the water. The crude product is triturated with ethyl acetate to dissolve the crude organic product. Chromatography on silica gel using methylene chloride:methanol:hexanes (5:1:5) gave 76 mg (41%).

$^1$Hnmr (CDCl$_3$, TMS) 1.27 (t, 6H), 1.51 (s, 6H), 1.91 (t, 2H), 2.35 (s, 3H), 2.85 (t, 2H), 3.62 (s, 2H), 4.03 (m, 4H), 4.91 (s, 2H), 7.88 (s, 1H).

$^{31}$P NMR (H-decoupled, CDCl$_3$): 31.00 (s).

This structure can be represented by formula XIX:

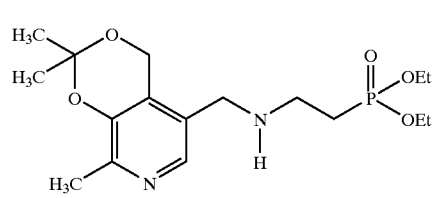

XIX

Example 16

Synthesis of ($\alpha^4$,3-O-isopropylidene-3-hydroxy-4-hydroxymethyl-2-methyl-5-pyridyl)-3-azabutylphosphonic Acid The product of Example 15, of formula XIX (280 mg, 0.75 mmol) was stirred in a mixture of acetonitrile (6 mL) and trimethylsilylbromide (TMSBr) (574 mg, 3.75 mmol) overnight at room temperature. The solvent was evaporated and the crude product was purified by chromatography on silica gel using dichloromethane:methanol:water (65:35:6) giving 188 mg (91%).

$^1$H NMR (D$_2$O) 1.65 (s, 6H), 2.02 (m,2H), 2.42 (s,3H), 3.40 (m, 2H), 4.24 (s, 2H), 5.12 (s,2H),8.11 (s, 1H).

$^{31}$p NMR (H-decoupled, D$_2$O): 18.90 (s).

This structure can be represented by formula XX:

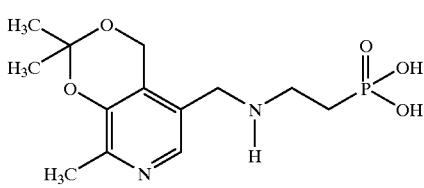

XX

Example 17

Synthesis of (3-hydroxy-4-hydroxymethyl-2-methyl-5-pyridyl)-3-azabutylphosphonic Acid The product of Example 16, of formula XX (168 mg, 0.53 mmol) was dissolved in acetic acid (80% in water, 10 mL) and heated to 60° C. for 5 hours. The solvent was removed by evaporation using toluene to codistill the water. The crude product was purified by chromatography on C-18 reverse phase silica gel using methanol:water (4:1) as eluent to give 57 mg (39%).

$^1$H NMR (D$_2$O) 2.05 (m, 2H), 2.52 (s, 3H), 3.38 (m, 2H), 4.42 (s, 2H), 4.96 (s, 2H), 7.87(s, 1H).

$^{31}$P NMR (H-decoupled, D$_2$O): 18.90 (s).

This structure can be represented by formula XXI:

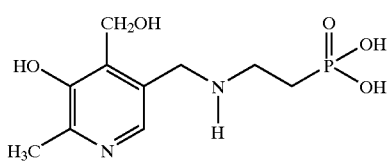

XXI

Example 18

Synthesis of Diethyl ($\alpha^4$,3-O-isopropylidene-3-hydroxy-4-hydroxymethyl-2-methyl-5-pyridyl)-2-hydroxyethylphosphonate To a solution of diethyl methyl phosphite (0.29 mL, 2 mmol) in THF (20 mL) was added BuLi (2.5 M in hexane, 0.88 mL, 2.2 mmol), followed by ($\alpha^4$,3-O-isopropylidene-3-hydroxy-4-hydroxymethyl-2-methyl-5-pyridyl)methanal (Kortynk et al., J. Org. Chem., 29, 574–579 (1964)) (414 mg, 2 mmol) and the reaction mixture stirred at –78° C. for two hours. The solution was evaporated, dissolved in dichloromethane (50 mL), washed with saturated, aqueous NaHCO$_3$, dried (MgSO$_4$), evaporated and purified by chromatography on silica gel using ethyl acetate:hexane (1:2) as eluent to give 625 mg (87%).

$^1$H NMR(CDCl$_3$, TMS) 1.33 (m, 6H), 1.54 (s, 6H), 2.20 (m, 2H), 2.38 (s, 3H), 4.12 (m, 4H), 4.94 (s, 2H), 4.94 (s, 2H), 5.04 (t, 1H), 8.02 (s, 1H).

$^3$P NMR (H-decoupled, CDCl$_3$): 29.03 (s).

This structure can be represented by formula XXII:

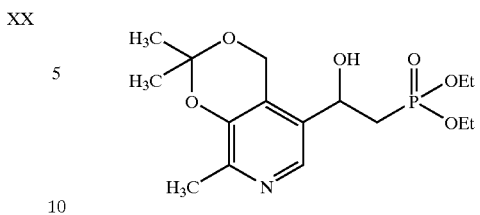

XXII

Example 19

Synthesis of Diethyl ($\alpha^4$,3-O-isopropylidene-3-hydroxy-4-hydroxymethyl-2-methyl-5-pyridyl)-2acetoxyethylphosphonate The product of Example 18, of structure XXII (300 mg, 0.84 mmol) was acetylated in pyridine (0.5 mL) and acetic anhydride (0.25 mL) at 0° C. for 5 minutes followed by 3 hours at room temperature. The solvent was removed by evaporation using toluene to codistill the solvents and the crude product was dissolved in dichloromethane (10 mL). This was washed with dilute HCl (10%, 5 mL), then saturated, aqueous NaHCO$_3$, dried (MgSO$_4$) and evaporated. Chromatography on silica gel using ethyl acetate:hexane (1:1) gave 258 mg (71%).

$^1$H NMR(CDCl$_3$, TMS) 1.21 (m, 6H), 1.54 (s, 6H), 2.03 (s,3H), 3.97 (m, 4H), 5.07 (dd, 2H), 5.83 (dd, 1H), 8.02 (s, 1H).

$^{31}$P NMR (H-decoupled, CDCl$_3$): 25.01 (s).

This structure can be represented by formula XXIII:

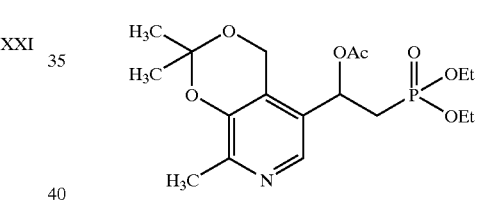

XXIII

Example 20

Synthesis of Diethyl ($\alpha^4$,3-O-isopropylidene-3-hydroxy-4-hydroxymethyl-2-methyl-5-pyridyl)-2-hydroxy-1,1-difluoroethylphosphonate To a solution of lithiumdiisopropylamide (LDA) (2.0 M, 1 mL, 2 mmol) in THF (5 mL) was added BuLi (0.5 M, 0.2 mL, 0.1 mmol). The mixture was cooled to –40° C. followed by the addition of diethyl difluoromethyl phosphonate (0.32 mL, 2 mmol) and the reaction mixture stirred at this temperature for 30 minutes. The solution was cooled to –78° C. and ($\alpha^4$,3-O-Isopropylidene-3-hydroxy-4-hydroxymethyl-2-methyl-5-pyridyl)methanal (Kortynk et al., J. Org. Chem., 29, 574–579 (1964)) (414 mg, 2 mmol) added in THF (2 mL). The solution was allowed to come to room temperature and stirred overnight. The solvent was evaporated, the residue dissolved in dichloromethane (20 mL), washed with saturated, aqueous NaHCO$_3$, dried (MgSO$_4$), and evaporated. Purification by chromatography on silica gel using ethyl acetate:hexane (2:1Y gave 528 mg (67%)

$^1$H NMR (CDCl$_3$, TMS) 1.35 (t, 3H), 1.38 (t, 3H), 1.52 (s, 3H), 1.55 (s, 3H), 2.39 (s,3H), 4.29 (m, 4H), 4.96 (dd, 3H), 8.09 (s, 1H).

$^{19}$F NMR (CDCl$_3$) –125.99 (ddd), –114.55 (ddd). $^{31}$P NMR (H-decoupled, CDCl$_3$): 7.22 (dd).

This structure can be represented by formula XXIV:

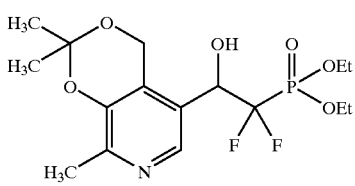

XXIV

Example 21

Synthesis of Diethyl (α⁴,3-O-isopropylidene-3-hydroxy-4-hydroxymethyl-2-methyl-5-pyridyl)-2-oxo-1,1-difluoroethylphosphonate The product of Example 20, of structure XXIV, (420 mg, 1.06 mmol) was dissolved in toluene (50 mL) and MnO$_2$ (651 mg, 636 mmol) added. The mixture was heated to 50° C. and stirred overnight. The solution was cooled, filtered (Celite) and the solvent evaporated to give the crude product. Purification by chromatography on silica gel ethyl acetate (1:2) gave 201 mg (48%).

$^1$H nmr (CDCl$_3$, TMS) 1.39 (q, 6H), 1.56 (d, 6H), 2.51 (s,3H), 4.34 (m, 4H), 5.08 (s, 2H), 8.88 (s, 1H).

$^{19}$F NMR (CDCl$_3$) −109.86 (d).

$^{31}$P NMR (H-decoupled, CDCl$_3$): 3.96 (t).

This structure can be represented by formula XXV:

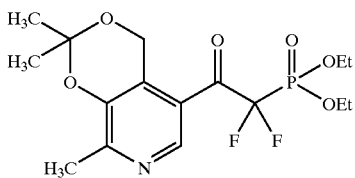

XXV

Example 22

Synthesis of Diethyl (3-hydroxy-4-hydroxymethyl-2-methyl-5-pyridyl)-2-hydroxy-1,1-difluoroethylphosphonate The product of Example 20, of structure XXIV (489 mg, 1.26 mmol) was dissolved in acetic acid (80% in water, 20 mL) and heated at 80° C. for 6 hours. The solvent was removed by evaporation by codistilling with toluene to remove last traces of acetic acid. The crude product was purified by chromatography on silica gel using dichloromethane:methanol:hexane (5:1:5) as eluent to give 171 mg (38%).

$^1$H NMR (CD$_3$OD) 1.32 (t, 3H), 1.37 (t, 3H), 2.43 (s,3H), 4.30 (m, 4H), 4.93 (dd, 2H), 5.39 (m, 2H), 8.07 (s,1H).

$^{19}$F NMR (CD$_3$OD) −125.55 (dd), −115.77 (dd).

$^{31}$P NMR (H-decoupled, MeOD): 7.82 (dd).

This structure can be represented by formula XXVI:

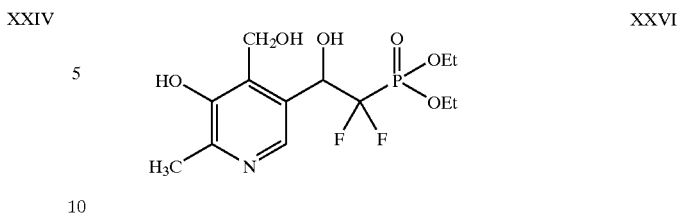

XXVI

Example 23

Synthesis of Diethyl (3-hydroxy-4-hydroxymethyl-2-methyl-5-pyridyl)-2-oxo-1,1-difluoroethylphosphonate The product of Example 21, of structure XXV (198 mg, 0.51 mmol) was dissolved in acetic acid (80% in water, 20 mL) and heated at 80° C. for 6 hours. The solvent was removed by evaporation by codistilling with toluene to remove last traces of acetic acid. The crude product was purified by chromatography on silica gel using dichloromethane:methanol:hexane (5:1:5) as eluent to give 25 mg (14%).

$^1$H NMR (CDCl$_3$, TMS) 1.38 (m, 6H), 2.37 (s,3H), 4.33 (m, 4H), 4.92 (s, 1H), 7.88 (s, 1H).

$^{19}$F (CDCl$_3$) −118.32 (d).

$^{31}$P NMR (H-decoupled, CDCl$_3$): 5.90 (t).

This structure can be represented by formula XXVII:

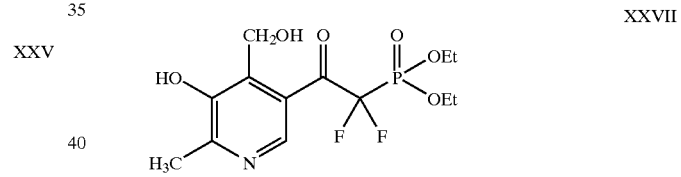

XXVII

Example 24

Synthesis of Diethyl (α⁴,3-O-isopropylidene-2-methyl-3-hydroxy-4-hydroxymethyl-5-pyridylmethyl)malonate To a solution of diethyl malonate (0.76 mL, 798 mg, 4.98 mmol) in tetrahydrofuran (THF) (5 mL) was added LDA (5 M, 1 mL, 5.0 mmol) and stirred at 0° C. for 5 minutes. (α⁴,3-O-isopropylidene-3-hydroxy-4-hydroxymethyl-2-methyl-5-pyridyl)methylbromide (Imperalli et al, J. Org. Chem., 60, 1891–1894 (1995)) (1.36 g, 5.0 mmol) in THF (5 mL) was added. The reaction was stirred for 2 hours at 0° C. The solvent was evaporated and the residue was dissolved in Et$_2$O. This was washed with water, dried (MgSO$_4$) and evaporated to give the crude product. Purification of the crude mixture by chromatography on silica gel column using diethyl ether:hexane (1:1) gave the malonate derivative 769 mg (44%).

$^1$H NMR (CDCl$_3$, TMS) 1.23 (t, 6H), 1.54 (s, 6H), 2.37 (s, 3H), 3.04 (d, 2H), 3.63 (t, 1H), 4.18 (q, 4H), 4.86 (s, 2H), 7.87 (s, 1H).

This structure can be represented by formula XXVIII:

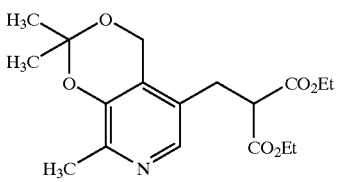

XXVIII

Example 25

Synthesis of Diethyl (2-methyl-3-hydroxy-4-hydroxymethyl-5-pyridylmethyl)malonate The product of Example 24, of structure XXVIII (769 mg, 2.18 mmol) was dissolved in acetic acid (80% in water, 25 mL) and heated at 80° C. for 3 hours. The solvent was removed by evaporation using toluene to codistill the solvents. The crude product was purified by chromatography on silica gel using ethyl acetate:hexane (4:1) as eluent to give 620 mg (91%).

$^1$H NMR (MeOD) δ 1.19 (t, 6H), 2.38 (s, 3H), 3.18 (d, J=7.6, 2H), 3.74 (t, J=7.7, 11H), 4.14 (q, 4H), 4.87 (s, 2H), 7.70 (s, 1H).

This structure can be represented by formula XXIX:

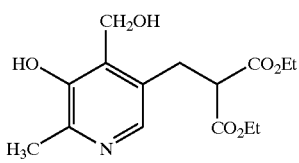

XXIX

Example 26

Synthesis of (2-methyl-3-hydroxy-4-hydroxymethyl-5-pyridylmethyl)malonic Acid

The product of Example 25, of structure XXIX (620 mg, 2.0 mmol) was dissolved in aqueous NaOH (2 M, 4 mL) and stirred at room temperature for 1 hour. The reaction was quenched by adding 6 N HCl to give pH 4 to 5. The solution was diluted with 95% ethanol, separated from the precipitated salts and evaporated to give 540 mg.

$^1$H NMR (DMSO) 2.58 (s, 3H), 3.24 (d, 2H), 3.81 (t, 1H), 4.78 (s, 2H), 8.05 (s, 1H).

This structure can be represented by formula XXX:

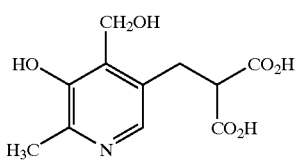

XXX

Example 27

Synthesis of Diethyl ((α$^4$,3-O-Isopropylidene-2-methyl-3-hydroxy-4-hydroxymethyl-5-pyridylmethylene)malonate (α$^4$,3-O-Isopropylidene-3-hydroxy-4-hydroxymethyl-2-methyl-5-pyridyl)methanal (Kortynk et al., J. Org. Chem., 29, 574–579 (1964)) (1.035 g, 5.5 mmol) was dissolved in benzene (10 mL) and, diethyl malonate (0.8 mL, 5 mmol), piperidine (0.08 mL) and acetic acid (0.09 mL) added. The solution was heated at 80° C. for 4 hours. The solution was diluted with diethyl ether (50 mL) and washed with dilute HCl, aqueous, saturated NaHCO$_3$, dried (MgSO$_4$) and evaporated to dryness. The crude product was purified by chromatography on silica gel using diethyl ether:hexane (1:2) as eluent to give 1.4 g (80%).

$^1$H NMR (CDCl$_3$) 1.24 (t, 3H), 1.33 (t, 3H), 1.55 (s, 6H), 2.42 (s, 3H), 4.27 (q, 2H), 4.31 (q, 2H), 4.83 (s, 2H), 7.52 (s, 1H), 8.06 (s, 1H).

This structure can be represented by formula XXXI:

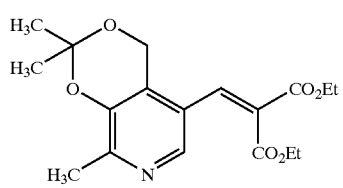

XXXI

Example 28

Synthesis of Diethyl 2-(α$^4$,3-O-Isopropylidene-2-methyl-3-hydroxy-4-hydroxymethyl-5-pyridyl)-1,2-difluoro-1,1-dicarbethoxyethane The product of Example 27, of structure XXXI ((354 mg, 1 mmol) was dissolved in acetonitrile (10 mL) and Pyr/HF (1 mL) added, followed by 1-(choromethyl)-4-fluoro-1,4-diazoniabicyclo[2.2.2]octane bis(tetrafluoroborate (Selectfluor reagent) (359 mg, 1 mmol). The reaction mixture was stirred at room temperature for 4 hours. The solution was diluted with diethyl ether (60 mL) and washed with water, NaHCO$_3$, and brine, dried (MgSO$_4$) and evaporated. Purification by chromatography on silica gel using diethyl ether:hexane (2:1) as eluent gave 90 mg (29%).

$^1$H NMR (CDCl$_3$, TMS) 1.21 (t, 3H), 1.26 (t, 3H), 2.48 (s, 3H), 3.7(d, 1H), 4.14–4.21(m, 4H), 5.01–5.03 (m, 2H), 5.03 (d,1H), 7.85 (s, 1H).

$^{19}$F NMR (CDCl$_3$) −181.33, −181.44.

This structure can be represented by formula XXXII:

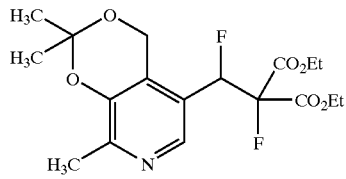

XXXII

Although embodiments of the invention have been described above, it is not limited thereto, and it will be apparent to persons skilled in the art that numerous modifications and variations form part of the present invention insofar as they do not depart from the spirit, nature, and scope of the claimed and described invention.

All publications, patents, and patent documents described herein are incorporated by reference as if fully set forth.

We claim:
1. A compound of the formula II

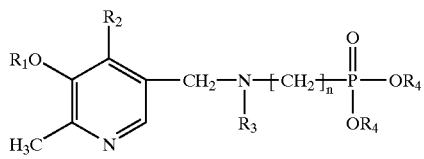

in which
R₁ is hydrogen or alkyl;
R₂ is —CHO, —CH₂OH, —CH₃ or —CO₂R₅ in which R₅ is hydrogen, alkyl, or aryl; or
R₂ is —CH₂-O-alkyl- (in which alkyl is covalently bonded to the oxygen at the 3-position instead of R₁);
R₃ is hydrogen, alkyl, aryl, or aralkyl;
R₄ is hydrogen, alkyl, aryl, aralkyl, or —CO₂R₆ in which R₆ is hydrogen, alkyl, aryl, or aralkyl; and
n is 1 to 6;
or a pharmaceutically acceptable acid addition salt thereof.

2. A compound according to claim 1, wherein R₁ is hydrogen.

3. A compound according to claim 1, wherein R₂ is —CH₂OH, or —CH₂-O-alkyl- in which alkyl is covalently bonded to the oxygen at the 3-position instead of R₁.

4. A compound according to claim 1, wherein R₃ is hydrogen.

5. A compound according to claim 1, wherein R₄ is alkyl or H.

6. A compound according to claim 1, wherein R₄ is ethyl.

7. A compound according to claim 1 selected from

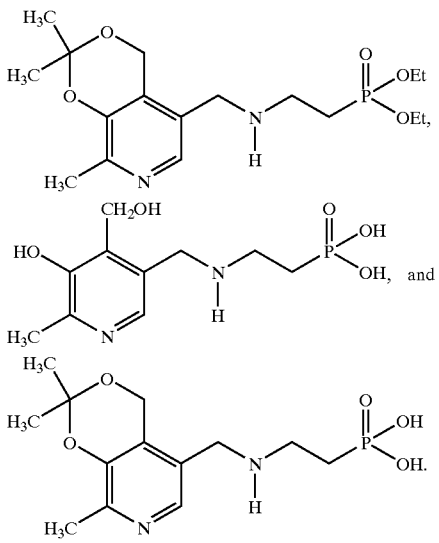

8. A pharmaceutical composition comprising a pharmaceutically acceptable carrier and a therapeutically effective amount of a compound according to claim 1.

9. A pharmaceutical composition of claim 8, wherein the pharmaceutical composition is in a form suitable for enteral or parenteral administration.

* * * * *

UNITED STATES PATENT AND TRADEMARK OFFICE
CERTIFICATE OF CORRECTION

PATENT NO. : 6,667,315 B2
DATED : December 23, 2003
INVENTOR(S) : Haque

It is certified that error appears in the above-identified patent and that said Letters Patent is hereby corrected as shown below:

<u>Title page,</u>
Item [56], References Cited, OTHER PUBLICATIONS, "Zempleni" reference, "utiliation" should read -- utilization --.

<u>Column 11,</u>
Lines 4-5, "butyl phosphite 15 or dibenzyl" should read -- butyl phosphite or dibenzyl --.

Lines 49-50, "formula 1,3,4-isopropylidenepyridoxine-5-al" should read -- formula I,3,4-isopropylidenepyridoxine-5-al --

<u>Column 16,</u>
Line 38, "formula 1" should read -- formula I --

<u>Column 21,</u>
Line 66, "Example I above," should read -- Example 1 above, --

<u>Column 33,</u>
Line 25, "(t, J=7.7, 11H)," should read -- (t, J=7.7, 1H), --

<u>Column 35,</u>
Line 33, "according to claim 1," should read -- according to claim 5, --

Signed and Sealed this

Fourth Day of May, 2004

JON W. DUDAS
*Acting Director of the United States Patent and Trademark Office*